Figure 1:
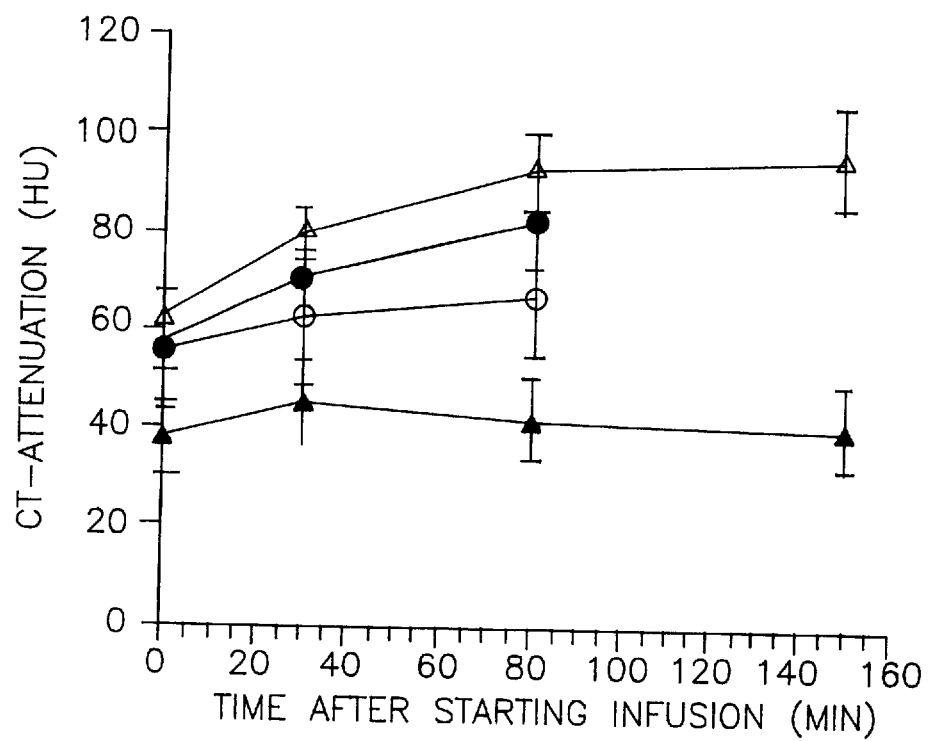

United States Patent [19]
Maier et al.

[11] Patent Number: 5,853,699
[45] Date of Patent: Dec. 29, 1998

[54] USE OF TETRA AZACYCLE COMPLEXES AS X-RAY DIAGNOSTIC AGENTS FOR THE LIVER AND GALLBLADDER

[75] Inventors: Franz-Karl Maier; Michael Bauer; Werner Krause; Ulrich Speck; Gabriele Schuhmann-Giampiere, all of Berlin; Andreas Mühler, Neuenhagen; Thomas Balzer; Wolf-Rüdiger Press, both of Berlin, all of Germany

[73] Assignee: Schering Aktiengesellschaft, Berlin, Germany

[21] Appl. No.: 565,397

[22] Filed: Nov. 30, 1995

Related U.S. Application Data

[63] Continuation-in-part of Ser. No. 387,408, Feb. 13, 1995, abandoned, which is a continuation-in-part of Ser. No. 351,086, Nov. 30, 1994, abandoned.

[51] Int. Cl.⁶ ................................. A61B 5/055
[52] U.S. Cl. ................ 424/9.363; 424/9.42; 534/16; 540/465; 540/471; 540/474; 514/184; 514/185; 514/836
[58] Field of Search ................ 424/9.42, 9.363; 514/184, 185, 836; 534/16; 540/465, 471, 474; 436/173; 128/653.4, 654

[56] References Cited

U.S. PATENT DOCUMENTS

| | | | |
|---|---|---|---|
| 3,994,966 | 11/1976 | Sundberg et al. | 260/518 R |
| 4,339,426 | 7/1982 | Meares et al. | 424/1 |
| 4,622,420 | 11/1986 | Meares et al. | 562/443 |
| 4,647,447 | 3/1987 | Gries et al. | 424/9.36 |
| 4,652,519 | 3/1987 | Warshawsky et al. | 435/7 |
| 4,672,028 | 6/1987 | Olson | 435/5 |
| 4,824,986 | 4/1989 | Gansow | 558/17 |
| 4,880,008 | 11/1989 | Lauffer | 128/654 |
| 4,899,755 | 2/1990 | Lauffer et al. | 128/654 |
| 4,916,246 | 4/1990 | Felder et al. | 556/1 |
| 5,057,302 | 10/1991 | Johnson et al. | 424/1.1 |
| 5,101,041 | 3/1992 | Troutner et al. | 548/518 |
| 5,137,711 | 8/1992 | Weber et al. | 424/9 |
| 5,198,208 | 3/1993 | Berg et al. | 424/1.1 |
| 5,250,285 | 10/1993 | Lauffer et al. | 424/9 |
| 5,316,756 | 5/1994 | Gries et al. | 424/9 |
| 5,318,771 | 6/1994 | Lauffer et al. | 424/9 |
| 5,358,704 | 10/1994 | Desreux et al. | 424/9 |
| 5,385,893 | 1/1995 | Kiefer | 424/9.363 |
| 5,399,340 | 3/1995 | Radüchel et al. | 424/9 |
| 5,403,572 | 4/1995 | Gries et al. | 424/9.363 |
| 5,419,893 | 5/1995 | Berg et al. | 424/9.363 |
| 5,419,894 | 5/1995 | Gries et al. | 424/1.65 |
| 5,482,700 | 1/1996 | Deutsch et al. | 424/9.364 |

FOREIGN PATENT DOCUMENTS

| | | |
|---|---|---|
| 0 165 716 | 12/1985 | European Pat. Off. . |
| 0 230 893 | 8/1987 | European Pat. Off. . |
| 0230893 | 8/1987 | European Pat. Off. . |
| 0 263 059 | 4/1988 | European Pat. Off. . |
| 0 299 795 | 1/1989 | European Pat. Off. . |
| 0 305 320 | 3/1989 | European Pat. Off. . |
| 0 315 220 | 5/1989 | European Pat. Off. . |
| 0405704 | 1/1991 | European Pat. Off. . |
| 1374979 | 11/1974 | United Kingdom . |
| 88/07521 | 10/1988 | WIPO . |
| 89/05802 | 6/1989 | WIPO . |
| 94/27644 | 12/1994 | WIPO . |
| 95/15319 | 6/1995 | WIPO . |

OTHER PUBLICATIONS

Havron et al. "Heavy Metal Particulate Contrast Materials for Computed Tomography of the Liver," Journal of Computer Assisted Tomography, 4(5):642–648 (Oct. 1980).

Seltzer et al., "Hepatic Contrast Agents for Computed Tomography: High Atomic Number Particulate Material," Journal of Computer Assisted Tomography, 5(3):370–374 (Jun. 1981).

Bloem et al., "Gd–DTPA as a Contrast Agent in CT," Radiology, 171(2):578–579 (May 1989).

Zwicker et al., "Kontrastgebung von Jod, Gadolinium und Ytterbium in der CT," Fortschr. Röntgenstr., 158(3):255–259 (1993).

Schmitz et al., "Evaluation of Gadobutrol in a Rabbit Model as a New Lanthanide Contrast Agent for Computed Tomography," Investigative Radiology, 30(11):644–649 (Nov. 1995).

Unger et al., "Ytterbium–DTPA—A Potential Intravascular Contrast Agent," Investigative Radiology, 21(10):802–807 (Oct. 1986).

Primary Examiner—Gary E. Hollinden
Attorney, Agent, or Firm—Millen, White, Zelano & Branigan, P.C.

[57] ABSTRACT

The disclosed metal complexes are suitable as contrast media for computer tomography of the liver and the biliary tracts.

23 Claims, 1 Drawing Sheet

USE OF TETRA AZACYCLE COMPLEXES AS X-RAY DIAGNOSTIC AGENTS FOR THE LIVER AND GALLBLADDER

This application is a continuation-in-part of U.S. application Ser. No. 08/387,408 filed Feb. 13, 1995, now abandoned, which is a continuation-in-part of Ser. No. 08/351,086, filed Nov. 30, 1994, now abandoned. The entirety of each of the above-identified applications is hereby incorporated by reference.

SUMMARY OF THE INVENTION

The invention relates to the use of metal complexes in diagnostic radiology of the liver and gallbladder using X-ray radiation, especially in computer tomography.

The early detection of focal liver diseases, especially liver metastases and liver tumors, is one of the most important diagnostic problems in oncology. Four imaging processes are available for this purpose: scintiscanning, ultrasonography, computer tomography, and magnetic resonance tomography. Each of these processes has specific advantages and disadvantages, none is really carried out optimally according to the present state of the art, and virtually every process would benefit from the presence of specific, compatible contrast media that can be administered intravenously [Hamed, R. K., Chezmar, J. L., Nelson, R. C.: Imaging of Patients with Potentially Resectable Hepatic Neoplasms. AJR 159, 1191–1194 (1992)].

Scintiscanning offers inadequate spatial resolution and is limited in its use by the insufficient or excessive (only usable for a few types of tumors) specificity of the radiopharmaceutical agents, so that it is not mentioned in the above-mentioned survey article. At this time, sonography is also an insufficiently reliable technique for detecting solid focal liver changes since the latter often are insufficiently distinguished from healthy liver tissue in their acoustic properties. Minor lesions in the liver tissue can be detected only during an operation after the liver is exposed and with use of high-frequency transducers. Magnetic resonance imaging (MRI) is able to detect the entire liver with good spatial resolution and, depending on the measuring method, also with good tissue differentiation. For MRI, well-tolerated effective contrast media can be administered intravenously in clinical testing, which further improve the uses of this imaging process. Disadvantages, however, are artifacts of movement in the high-resolution measuring process, which takes several minutes, and the high costs of the hardware itself; these factors limit its availability.

Computer tomography (CT) is actually the ideal technique for liver diagnosis. With modern hardware, the entire liver can be scanned within about 30 seconds with excellent spatial resolution. An individual liver layer takes about 1 second, so that movements caused by breathing and peristalsis play hardly any role. The costs of CT are considerably lower than those of MRI. The disadvantage of low tissue density resolution must be compensated for, however, by contrast media. With the contrast media now clinically available, there are the following possibilities:

1. The contrast media are intravenously injected or infused quickly and in large doses (50–200 g). For a few minutes there can, in individual cases, be a difference in contrast between the lesion and the normal liver tissue, which is due to the differences in the perfusion, the relative blood volume of the tissue, and the extracellular space. Only with the above-mentioned, very highspeed CT can this period of unequal distribution of the contrast media be exploited for diagnosis.

2. 4–6 hours after administration of at least 120 g of the usual urographic contrast media, improved contrast between the healthy liver parenchyma, which absorbs the contrast medium and focal liver lesions, which in most cases do not take up the contrast medium, is observed in a very small portion of patients. This technique, referred to as "late scan," however, is not sufficiently reliable and informative, so that it cannot be used routinely.

3. In the case of arterial hepatography, a catheter must be inserted into, e.g., the A. mesenterica;

the patient is then brought to the CT device, and the scan is performed while about 150 ml of contrast medium is infused. This technique is invasive, time-consuming, and costly, but at this time yields the most reliable data on the presence and location of liver metastases. This information is of decisive importance for the decision on the resectability of metastases. CT with arterial hepatography is therefore regularly performed pre-operatively despite the expense.

The effect of the above-described problems is that the X-ray contrast media now available are basically urographic products, which do not concentrate in the liver. Nevertheless, to produce some contrast, the liver is flooded by the blood stream with very large amounts of contrast media for a short time ("dynamic scan"), or an attempt is made to use the 1–2% of the contrast medium that is later found in the liver parenchyma in a portion of the patients ("late scan").

It can easily be seen that a need exists for improved diagnosis of focal liver lesions since the existing processes are too ineffective, too costly, or too burdensome for the patients. Therefore, over decades, innumerable attempts have been made to develop liver-specific X-ray contrast media that can be administered intravenously. Of the large number of preparations tested, only a few can be mentioned (see also Tables 1–2): thorotrast (colloidal suspensions of thorium oxide) produced excellent liver contrast, but was not excreted. The α-emitter thorium caused liver tumors decades after administration. In 1940, Schering marketed the preparation hepatoselectan, an emulsion of very fine droplets of a triiodinated oil. Because of acute side effects, it had to be taken off the market. Successor products from other companies and research groups (EOE-13, AG-60-99, etc.) were given up even during the clinical tests because of the same problems.

TABLE 1

| Emulsions | | | |
|---|---|---|---|
| Designation | Company | Examiner | Status |
| Oil Emulsions i.v. | | | |
| AG 60–99 | Guerbet | Lamarque | 100 patients, terminated |
| EOE 13 | — | Vermess | Several hundred patients, terminated |
| EOE 14 | Abbott | — | Only pre-clinical |
| Perfluoroocty lbromide | Boehringer Ingelheim | Bruneton | Clinical test terminated |
| Intraiodol | — | Lunderquist | Clinical test terminated |

TABLE 1-continued

Emulsions

| Designation | Company | Examiner | Status |
|---|---|---|---|
| Oil Emulsions, I.A. | | | |
| Lipiodol | — | numerous users | not approved |

TABLE 2

Liposomes

| Liposomes Designation | Company | Examiner | Status |
|---|---|---|---|
| Amidotrizoate or iotrolan | — | Rosenberg | High rate of side effects in humans, not approved |
| Iopromide | Schering | Krause | Animal experiments |
| Iopamidol | Bracco | Musu | Animal experiments |
| Ioxaglat | Guerbet | Corot | Animal experiments |

In addition to a considerable number of pharmaceutical problems, all individual preparations (suspensions, emulsions, liposomes) have the disadvantage, at the high dosages (5–20 g) used for diagnostic radiology, of causing characteristic side effects that are difficult to avoid. In the 1970s and the early 1980s, great efforts were therefore made to find water-soluble X-ray contrast media that accumulate in the liver—sufficiently for CT. Such substances were provided with up to 6 iodine atoms per molecule and, largely for this reason, were very effective and well-tolerated in some cases in animal experiments. Great differences in effectiveness were noticeable from individual animal species to individual species. Until now, however, none of the iodine-containing water-soluble contrast media examined reached a high enough concentration in the liver in humans to make development for CT appear promising. A characteristic example of the many failed tests was published by Mutzel, W., Wegener, O. H., Souchon, R. and Weinmann, H.-J., Water-Soluble Contrast Agents for Computed Tomography of the Liver: Experimental Studies in Dog. In Amiel (edt.): Contrast Media in Radiology, Lyon 1981, Springer Verlag Berlin Heidelberg New York 1982, pp. 320–323, Table 1. Also in this case, insufficient liver contrast was found in humans, unlike what was found in many types of animals.

Intravenous cholegraphic agents, such as iotroxinate and ioglycamate, accumulate selectively in the liver. This process is very limited in capacity, however. At a concentration corresponding to 5 µg of iodine per ml of plasma, a 5-fold concentration in the liver is achieved, at a concentration of 50 µg of iodine/ml barely a 2-fold concentration is reached, and at 500 µg of iodine/ml of plasma, the concentration in the liver is considerably lower than in the plasma and therefore largely of no value diagnostically since differentiation between actively accumulating tissue and mere perfusion is impossible. Computer tomography, however, detects with sufficient reliability iodine only at concentrations starting from about 1 mg/ml (Speck, U., Mützel, W., Herz-Hübner, U., Siefert, H. M. Pharmakologie der Iotroxinsäure, eines neuen intravenösen Cholegraphicums I. Pharmakokinetik und Radiologie beim Tier. [Pharmacology of Iotroxic Acid, a New Intravenous Cholegraphic Agent I. Pharmacokinetics and Radiology in Animals]. Drug. Res. 28, 2143–2149 (1978).

Thus, it still can be maintained that a need exists for preferably water-soluble and therefore pharmaceutically readily characterizable, stable, compatible, specific X-ray contrast media that are effective at not too high a dose and that, despite decades of efforts, no single product has thus far been marketed or else is only in a promising stage of clinical testing. Because of the unpredictable species dependence on intake, concentration and excretion through the liver via animal-experiment tests, it is difficult to find such preparations; also, after many disappointing results in humans, animal-experiment findings, by themselves, can not always provide a reliable indication of the suitability or unsuitability of a substance or family of substances.

Metal-containing contrast media for magnetic resonance imaging also absorb X-rays. An attempt has therefore been made, in individual cases, to use these substances for computer tomography (Schild, H. H. et al.: Gadolinium DTPA (Magnevist®) as Contrast Media for Arterial DSA. Fortschr. Röntgenstr. [X-Ray Radiation Research], 160, 218–221 (1994); Quinn, A. D. et al.: Gd-DTPA: An Alternative Contrast Medium for CT. J. Comput. Assist. Tomogr. 18, 634–636 (1994)). It is to be taken into consideration that the previously available metal complexes bond only one opacifying metal ion per molecule, while the iodinated X-ray contrast media contain 3 or 6 iodine atoms. Despite the higher effectiveness of some metal ions compared to iodine (Zwicker, C., Langer, M., Langer, R., Keske, U. Comparison of Iodinated and Non-iodinated Contrast Media in Computed Tomography. Invest. Radiol. 26, 162–164 (1991), the iodinated contrast media thus far have not been replaced by metal chelates in any relevant indication.

Disadvantages, however, are the significantly lower content of X-ray-absorbing element in the molecules (iodinated X-ray contrast media: 3 or 6 iodine atoms/molecule; MRI contrast media: 1 metal ion/molecule). The opacification is correspondingly weak, so that the metal complexes were used almost solely for experimental studies in radiology. In MRI, low concentrations of metal ions are sufficient since the latter affect the quickly exchanging protons of water, while in radiology the metal itself must be made visible.

An object of the invention therefore is to determine, from the known pharmaceutical substances based on metal chelates that are suitable for imaging diagnosis and metal chelates similar thereto, those substances which are suitable for the production of contrast media for diagnostic radiology, especially computer tomography of the liver and biliary tracts.

Upon further study of the specification and appended claims, further objects and advantages of this invention will become apparent to those skilled in the art.

These objects are achieved by the invention as described below.

It has been found that metal complexes containing a metal of atomic numbers 39–42, 44–51 or 56–83 and a complexing agent are suitable for the production of contrast media for use in contrast-enhanced computer tomography of the liver and the biliary tracts.

It was surprising that with certain groups of metal chelates, despite clearly worse preconditions on the part of the radiation-absorbing action per molecule, an absorption of the x rays in the liver, completely satisfactory for computer tomography, was achieved for the first time in humans, without in this case approximately as high dosages having to be used, as is the case in the unspecific iodinated x-ray contrast media. Simultaneously, it was shown that the concentration in the liver takes place quickly and is sustained long enough for the computer-tomographic diagnosis process. The administration can take place non-invasively intravenously. The compatibility is very good in the required dose range.

In general, acid metal complexes with a molecular weight under 1500 D or is at most 1500 D, which contain at least one metal ion with the atomic number 39–42, 44–51 or 56–83, suitable for the x-ray absorption, are suitable. Preferred are those complexes that are characterized by two carboxyl groups not involved in the complexing of the opacifying element; the substances are to contain in the molecule at least one structural element, consisting of at least three C atoms, which is more lipophilic than gadolinium-DTPA or the entire lipophilia (distribution coefficient of butanol/tris-buffer pH 7.6>0.0002) of the molecules has to be higher than that of the gadolinium-DTPA, as well as one or more metal ions of atomic numbers 56–83 in a firm complex-bound way, and the binding constant is at least $10^{14}$ or exceeds $10^{14}$. Such substances and their production are described, i.a., in EP 0 405 704; EP 0 230 893; U.S. Pat. No. 4,880,008; U.S. Pat. No. 4,899,755; U.S. Pat. No. 5,250,285 and U.S. Pat. No. 5,318,771.

Additional information about reaction processes and reaction conditions is published in the following publications:

Synthesis of ethers, in particular phenolic ethers:
  Houben-Weyl, Band VI/3, Georg Thieme Verlag, Stuttgart, 1965
Synthesis of amines and amino acid derivatives:
  Houben-Weyl, Band XI/ 1, Georg Thieme Verlag, Stuttgart, 1957, Houben-Weyl, Band XI/2, George thieme Verlag, Stuttgart, 1958
Synthesis of Alkyl halides:
  Houben-Weyl, Band V/3, Georg Thieme Verlag, Stuttgart, 1962, Houben-Weyl, Band V/4, Georg Thieme Verlag, Stuttgart, 1960
Synthesis of carboxylic acids and derivatives thereof:
  Houben-Weyl, Band VIII, Georg Thieme Verlag, Stuttgart, 1952
Synthesis of sulfonic acid derivatives:
  Houben-Weyl, Band IX, Georg Thieme Verlag, Stuttgart, 1955
Reductive amination:
  C. F. Lane, Synthesis 135 (1975)
Synthesis of DTPA derivatives:
  M. A. Williams, H. Rapoport, J. Org. Chem., 58, 1151 (1993)

Preferred substances according to the invention are described by general formulas I to XIII:
Formula I

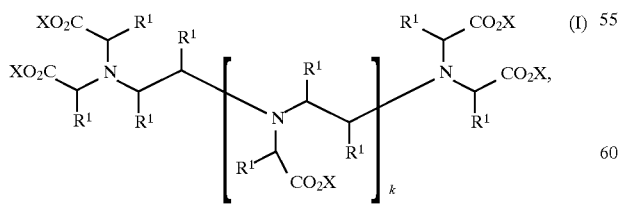

wherein
  X, independently of one another, stand for a hydrogen atom, or for a metal ion equivalent of an element of atomic numbers 39–42, 44–51 or 56–83,
  k stands for the numbers 0, 1 or 2, and
  $R^1$, independently of one another, stand for a hydrogen atom or a radical of formula Ia

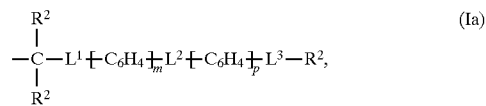

wherein
  m, p stand for the numbers 0 or 1,
  $R^2$, independently of one another, stand for a hydrogen atom or a branched or unbranched, saturated or unsaturated $C_1$–$C_6$ hydrocarbon radical, and
  $L^1$, $L^2$, $L^3$ each stand for a direct bond, an oxygen atom, a sulfur atom, an —N(H) or —N($R^2$) group or a $C_1$–$C_{10}$ alkylene chain, which optionally is interrupted by an oxygen or a sulfur atom, an —N(H) or an —N($R^2$) group,
in which if m and/or p is equal to zero, no two or more heteroatoms must be directly connected with one another and
in which free carboxyl groups not used for complexing can also be present as salts of physiologically compatible cations or as an amide of formula

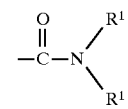

wherein
  $R^1$ has the above-indicated meaning;
Formula II

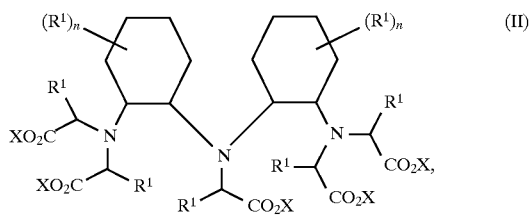

wherein
  X, independently of one another, stand for a hydrogen atom or for a metal ion equivalent of an element of atomic numbers 39–42, 44–51 or 56–83,
  n stands for the numbers 0, 1 or 2, and
  $R^1$, independently of one another, stand for a hydrogen atom or a radical of formula Ia,

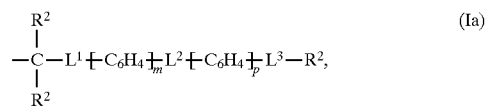

wherein
  m, p stand for the numbers 0 or 1,
  $R_2$, independently of one another, stand for a hydrogen atom or a branched or unbranched, saturated or unsaturated $C_1$–$C_6$ hydrocarbon radical, and
  $L^1$, $L^2$, $L^3$ each stand for a direct bond, an oxygen atom, a sulfur atom, an —N(H)— or —N($R^2$) group or a $C_1$–$C_{10}$ alkylene chain, which optionally is interrupted by an oxygen or a sulfur atom, an —N(H) or an —N($R^2$) group,
in which if m and/or p is equal to zero, no two or more heteroatoms must be connected directly with one another, in which the six-membered carbon rings present in formula II can also be aromatic, and in which free carboxyl groups not used for complexing can also be present as salts of physiologically compatible cations or as an amide of formula

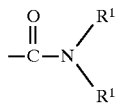

in which

R$^1$ has the above-indicated meaning;

Formula III

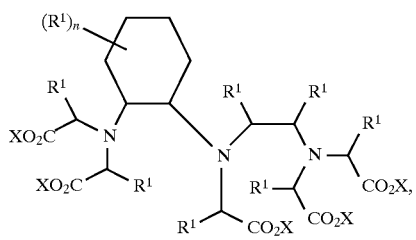

wherein

X, independently of one another, stand for a hydrogen atom or for a metal ion equivalent of an element of atomic numbers 39–42, 44–51 or 56–83, n stands for the numbers 0, 1 or 2, and, R$^1$, independently of one another, stand for a hydrogen atom or a radical of formula Ia

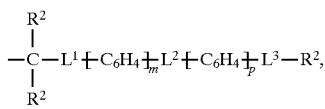

wherein m, p stand for the numbers 0 or 1,

R$^2$, independently of one another, stand for a hydrogen atom or a branched or unbranched, saturated or unsaturated C$_1$–C$_6$ hydrocarbon radical, and L$^1$, L$^2$, L$^3$ each stand for a direct bond, an oxygen atom, a sulfur atom, an —N(H) or —N(R$^2$) group or a C$_1$–C$_{10}$ alkylene chain, which optionally is interrupted by an oxygen or a sulfur atom, an —N(H) or an —N(R$^2$) group, in which if m and/or p is equal to zero, no two or more heteroatoms must be connected directly with one another, in which the six-membered carbon ring present in formula III can also be aromatic, and in which free carboxyl groups not used for complexing also can be present as salts of physiologically compatible cations or as an amide of formula

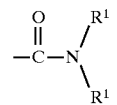

wherein

R$^1$ has the above-indicated meaning;

Formula IV

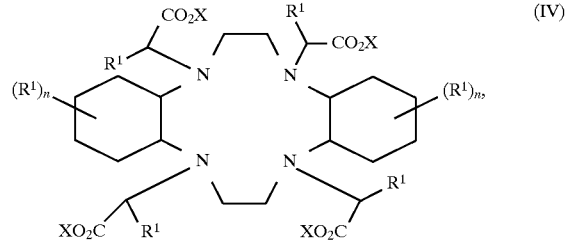

wherein

X, independently of one another, stand for a hydrogen atom or for a metal ion equivalent of an element of atomic numbers 39–42, 44–51 or 56–83, n stands for the numbers 0, 1 or 2, and R$^1$, independently of one another, stand for a hydrogen atom or a radical of formula Ia

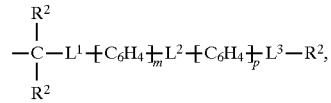

wherein m, p stand for the numbers 0 or 1,

R$^2$, independently of one another, stand for a hydrogen atom or a branched or unbranched, saturated or unsaturated C$_1$–C$_6$ hydrocarbon radical, and L$^1$, L$^2$, L$^3$ each stand for a direct bond, an oxygen atom, a sulfur atom, an —N(H) or —N(R$^2$) group or a C$_1$–C$_{10}$ alkylene chain, which optionally is interrupted by an oxygen or a sulfur atom, an —N(H) or an —N(R$^2$) group, in which if m and/or p is equal to zero, no two or more heteroatoms must be directly connected with one another, in which the six-membered carbon rings present in formula IV can also be aromatic, and, in which free carboxyl groups not used for complexing can also be present as salts of physiologically compatible cations or as an amide of formula

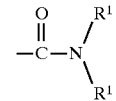

wherein

R$^1$ has the above-indicated meaning;

Formula V

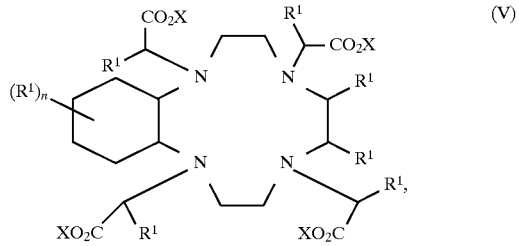

wherein

X, independently of one another, stand for a hydrogen atom or for a metal ion equivalent of an element of atomic numbers 39–42, 44–51 or 56–83, n stands for the numbers 0, 1 or 2, and $R^1$, independently of one another, stand for a hydrogen atom or a radical of formula Ia $$-\overset{R^2}{\underset{R^2}{C}}-L^1+C_6H_4\xrightarrow{}_m L^2+C_6H_4\xrightarrow{}_p L^3-R^2, \quad \text{(Ia)}$$

wherein
  m, p stand for the numbers 0 or 1,
  $R^2$, independently of one another, stand for a hydrogen atom or a branched or unbranched, saturated or unsaturated $C_1$–$C_6$ hydrocarbon radical, and
  $L^1$, $L^2$, $L^3$ each stand for a direct bond, an oxygen atom, a sulfur atom, an —N(H) or —N($R^2$) group or a $C_1$–$C_{10}$ alkylene chain, which optionally is interrupted by an oxygen or a sulfur atom, an —N(H) or an —N($R^2$) group,
in which if m and/or p is equal to zero, no two or more heteroatoms must be directly connected with one another, in which the six-membered carbon ring present in formula V can also be aromatic, and
in which free carboxyl groups not used for completing can also be present as salts of physiologically compatible cations or as an amide of formula $$-\overset{O}{\underset{}{C}}-N\overset{R^1}{\underset{R^1}{\diagdown}}$$

wherein
  $R^1$ has the above-indicated meaning;
Formula VI

<br>

$$\text{(VI)}$$
(cyclen-type macrocycle with four N atoms, bearing $CO_2X$, $R^1$, $XO_2C$ substituents)

wherein
  X, independently of one another, stand for a hydrogen atom, or for a metal ion equivalent of an element of atomic numbers 39–42, 44–51 or 56–83, and
  $R^1$, independently of one another, stand for a hydrogen atom or a radical of formula Ia $$-\overset{R^2}{\underset{R^2}{C}}-L^1+C_6H_4\xrightarrow{}_m L^2+C_6H_4\xrightarrow{}_p L^3-R^2, \quad \text{(Ia)}$$

wherein
  m, p stand for the numbers 0 or 1,
  $R^2$, independently of one another, stand for a hydrogen atom or a branched or unbranched, saturated or unsaturated $C_1$–$C_6$ hydrocarbon radical, and
  $L^1$, $L^2$, $L^3$ each stand for a direct bond, an oxygen atom, a sulfur atom, an —N(H) or —N($R^2$) group or a $C_1$–$C_{10}$ alkylene chain, which optionally is interrupted by an oxygen or a sulfur atom, an —N(H) or an —N($R^2$) group,
in which if m and/or p is equal to zero, no two or more heteroatoms must be directly connected with one another and
in which free carboxyl groups not used for complexing can also be present as salts of physiologically compatible cations or as an amide of formula $$-\overset{O}{\underset{}{C}}-N\overset{R^1}{\underset{R^1}{\diagdown}}$$

wherein
  $R^1$ has the above-indicated meaning;
Formula VII $$\text{(VII)}$$
(linear polyamine chain structure with Ar, $R^1$, $CO_2X$ substituents, repeated k times)

wherein
  X, independently of one another, stand for a hydrogen atom, or for a metal ion equivalent of an element of atomic numbers 39–42, 44–51 or 56–83,
  k stands for the numbers 0, 1 or 2, and
  $R^1$, independently of one another, stand for a hydrogen atom or a radical of formula Ia $$-\overset{R^2}{\underset{R^2}{C}}-L^1+C_6H_4\xrightarrow{}_m L^2+C_6H_4\xrightarrow{}_p L^3-R^2, \quad \text{(Ia)}$$

wherein
  m, p stand for the numbers 0 or 1,
  $R^2$, independently of one another, stand for a hydrogen atom or a branched or unbranched, saturated or unsaturated $C_1$–$C_6$ hydrocarbon radical, and
  $L^1$, $L^2$, and $L^3$ each stand for a direct bond, an oxygen atom, a sulfur atom, an —N(H) or —N($R^2$) group or a $C_1$–$C_{10}$ alkylene chain, which optionally is interrupted by an oxygen or a sulfur atom, an —N(H) or an —N($R^2$) group,
in which if m and/or p is equal to zero, no two or more heteroatoms must be directly connected with one another and
in which free carboxyl groups not used for complexing can also be present as salts of physiologically compatible cations or as an amide of formula $$-\overset{O}{\underset{}{C}}-N\overset{R^1}{\underset{R^1}{\diagdown}}$$

wherein
  $R^1$ has the above-indicated meaning, and
  Ar, independently of one another, stand for a saturated or unsaturated, optionally bicyclic, $C_5$–$C_{10}$ ring, which optionally is interrupted by one to two oxygen, sulfur and/or nitrogen atoms, and
  optionally is substituted by one to three phenyl, pyridyl, HO, HS, HOOC, $R^1$OOC, $R^1$O, $R^1$NHOC, $R^1$CONH, $R^1$ and/or $H_2N$ groups, which further optionally contains one to three carbonyl, thiocarbonyl and/or imino groups;

Formula VIII

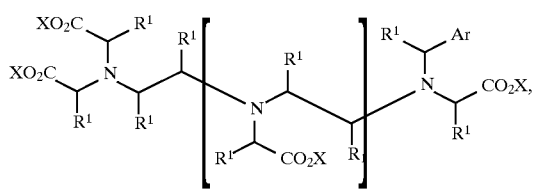

wherein

X, independently of one another, stand for a hydrogen atom, or for a metal ion equivalent of an element of atomic numbers 39–42, 44–51 or 56–83, k stands for the numbers 0, 1 or 2, and $R^1$, independently of one another, stand for a hydrogen atom or a radical of formula Ia

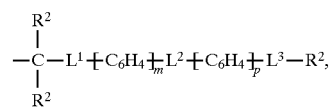

wherein m, p stand for the numbers 0 or 1, $R^2$, independently of one another, stand for a hydrogen atom or a branched or unbranched, saturated or unsaturated $C_1$–$C_6$ hydrocarbon radical, and $L^1$, $L^2$, $L^3$ each stand for a direct bond, an oxygen atom, a sulfur atom, an —N(H) or —N($R^2$) group or a $C_1$–$C_{10}$ alkylene chain, which optionally is interrupted by an oxygen or a sulfur atom, an —N(H) or an —N($R^2$) group, in which if m and/or p is equal to zero, no two or more heteroatoms must be directly connected with one another and in which free carboxyl groups not used for complexing can also be present as salts of physiologically compatible cations or as an amide of formula

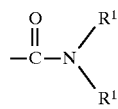

wherein $R^1$ has the above-indicated meaning, and

Ar, independently of one another, stand for a saturated or unsaturated, optionally bicyclic, $C_5$–$C_{10}$ ring, which optionally is interrupted by one to two oxygen, sulfur and/or nitrogen atoms, and optionally is substituted by one to three phenyl, pyridyl, HO, HS, HOOC, $R^1$OOC, $R^1$O, $R^1$NHOC, $R^1$CONH, $R^1$ and/or $H_2N$ groups, which further optionally contains one to three carbonyl, thiocarbonyl and/or imino groups;

Formula IX

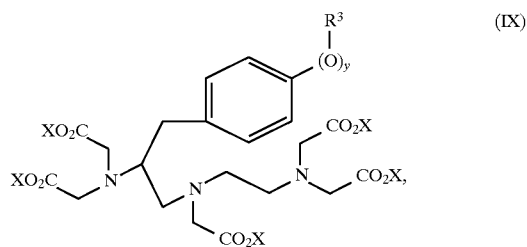

wherein

X, independently of one another, stand for a hydrogen atom, or for a metal ion equivalent of an element of atomic numbers 39–42, 44–51 or 56–83, y stands for the number zero or one and $R^3$ stands for a $C_1$–$C_5$ alkyl radical or a benzyl radical:

Formula X

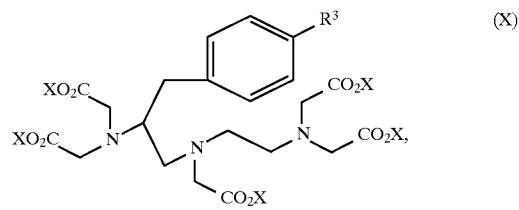

wherein

X, independently of one another, stands for a hydrogen atom, or for a metal ion equivalent of an element of atomic numbers 39–42, 44–51 or 56–83, $R^3$ stands for a methyl, ethyl, n-propyl, n-butyl or a benzyl radicals;

Formula XI

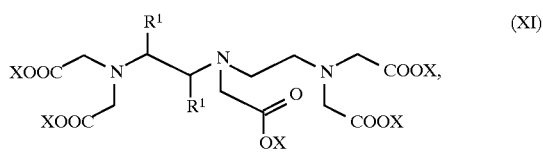

wherein,

X, independently of one another, in each case stands for a hydrogen atom or a metal ion equivalent of an element of atomic numbers 44–51 or 56–83, one of radicals $R^1$ stands for a radical of formula —$CH_2$—$C_6H_4$—(O)$_r$—$R^2$, in which the aromatic ring of this radical $R^1$ can be substituted in the ortho, meta, or para position, and other radical $R^1$ stands for hydrogen, $R^2$ stands for a hydrocarbon radical that contains 1–6 carbon atoms and 0–2 oxygen atoms, a phenyl radical or a benzyl radical, or $R^2$ stands for hydrogen and r stands for the number zero or one, in which carboxyl groups can also be present as amides, or salts thereof with physiologically compatible inorganic and/or organic cations, e.g., for charge neutralization;

Formula XII

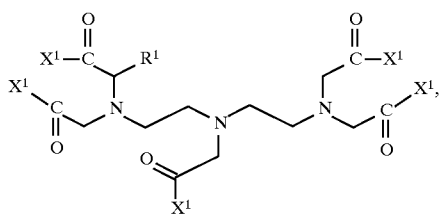

in which

R¹ stands for a radical of formula Ib

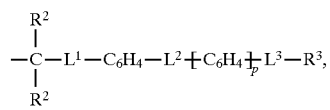

in which p stands for number 0 or 1,

R², independently of one another, in each case stands for a hydrogen atom or a branched or unbranched, saturated or unsaturated $C_1$–$C_6$ hydrocarbon radical, R³ stands for a hydrogen atom or a branched or unbranched, saturated or unsaturated $C_1$–$C_6$ hydrocarbon radical or a carboxyl group, L¹ stands for a direct bond or a $C_1$–$C_4$ alkylene chain, L² and L³, respectively independently of one another, each stand for a direct bond, an oxygen atom, a sulfur atom or a $C_1$–$C_{10}$ alkylene chain, which optionally is interrupted by one to three oxygen atoms and/or one to three sulfur atoms, and two or more heteroatoms must not be directly bonded with one another, and X¹, independently of one another, in each case stands for a group O—X² or N(R⁴)R⁵, R⁴ and R⁵, independently of one another, in each case stand for a hydrogen atom, $C_1$–$C_6$ alkyl, or for a group R¹ or R⁴ and R⁵ together, with inclusion of the common amide nitrogen atom, form a four- to eight-membered ring, which can in addition, optionally, contain up to two additional oxygen atoms and/or up to two carbonyl or sulfonyl groups, and X², independently of one another, in each case stands or a hydrogen atom or a metal ion equivalent of an element of atomic numbers 39–51 or 57–83, as well as salts thereof with the physiologically compatible inorganic and/or organic cations, for example, for charge equalization;

Formula XIII

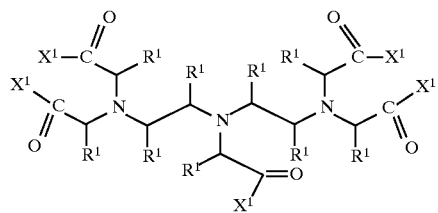

in which 5, 6 or 7 of the R¹ radicals stand for hydrogen and the other R¹ radicals, independently of one another, stand for a radical of formula Ic

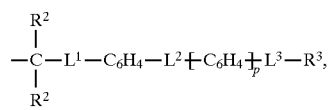

in which p stands for number 0 or 1,

R², independently of one another, in each case stands for a hydrogen atom or a branched or unbranched, saturated or unsaturated hydrocarbon $C_1$–$C_6$ radical, R³ stands for a hydrogen atom or a branched or unbranched, saturated or unsaturated $C_1$–$C_6$ hydrocarbon radical or a carboxyl group, L¹ stands for a direct bond, a sulfur atom, a $C_1$–$C_4$ alkylene chain or L¹ stands for a $C_1$–$C_4$ alkylene chain that is interrupted by a sulfur atom, L² and L³, respectively independently of one another, each stand for a direct bond, an oxygen atom, a sulfur atom or a $C_1$–$C_{10}$ alkylene chain, which optionally is interrupted by one to three oxygen atoms and/or one to three sulfur atoms, wherein in $L^2$—$[C_6H_4]_p$—$L^3$ two or more heteroatoms are not directly bonded to one another and X¹, independently of one another, in each case stands for a group o—X² or N(R⁴)R⁵, R⁴ and R⁵, independently of one another, stand for a hydrogen atom, $C_1$–$C_6$ alkyl or for a radical R¹ or R⁴ and R⁵ together, with inclusion of the common amide nitrogen atom, form a four- to eight-membered ring, which can in addition optionally contain up to two oxygen atoms and/or up to two carbonyl or sulfonyl groups, X², independently of one another, in each case stands for a hydrogen atom or a metal ion equivalent of an element of atomic numbers 39–51 or 57–83, as well as salts thereof with physiologically compatible inorganic and/or organic cations for, for example, charge neutralization.

The symbol

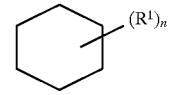

stands for a $C_6$-ring, which can be saturated, unsaturated or aromatic, and which is substituted n-fold by group $R_1$.

As radicals of general formulas Ia, Ib and Ic, there can be mentioned as examples: benzyl, methoxybenzyl, ethoxybenzyl, propoxybenzyl, isopropoxybenzyl, butoxybenzyl, isobutoxybenzyl, tert.-butoxybenzyl, pentoxybenzyl, benzyloxybenzyl, methylbenzyl, ethylbenzyl, propylbenzyl, butylbenzyl, pentylbenzyl and benzylbenzyl radicals. Preferred radicals are methoxybenzyl, ethoxybenzyl and butylbenzyl, especially preferred is the ethoxybenzyl radical.

Of the metal ions, the lanthanides are preferred. In measurements under actual conditions (see Example 1), holmium, erbium, and ytterbium have proven more suitable than the elements gadolinium and dysprosium, which are commonly used in MRI. Because of its high price, thulium seems less suitable from the economic standpoint, but is still suitable in principle. Other elements, however, can also be used. In particular, chelate compounds of lutetium, praseodymium, cerium, hafnium, lead, and bismuth also exhibit especially advantageous properties.

It is often the case that the complexing agent exhibits more acid functions than the complexed metal has positive elementary charges. Thus, for example, the 3,6,9-triaza-3,6,9-tris-(carboxymethyl)-2-(4-ethoxybenzyl)-undecanedioic acid described in Example 1 has five acid groups, while the dysprosium is present in dysprosium oxide ($Dy_2O_3$) in oxidation stage +III. In the case of complexing, thus only three of the five protons of the acid are neutralized. A complex which contains two protons that can be dissociated, an acid complex, is thus formed. In aqueous solution, two protons and one dianion—formed from the metal and the complexing agent—are thus present. For many purposes, it is advantageous to exchange the protons for other physiologically compatible cations (neutralization), so that a salt is formed. As physiologically compatible cations, sodium$^+$, calcium$^{2+}$, magnesium$^{2+}$ and zinc$^{2+}$ as well as cations of organic bases, such as meglumine, glucosamine, arginine, ornithine, lysine and ethanolamine, can be mentioned as examples.

For use in accordance with invention, especially the following compounds are extremely well suited:

Gadolinium(III) complex of 3,6,9-triaza-3,6,9-tris(carboxymethyl)-4-(4-ethoxy-benzyl)-undecanedioic acid,
Ytterbium(III) complex of 3,6,9-triaza-3,6,9-tris(carboxymethyl)-4-(4-ethoxy-benzyl)-undecanedioic acid,
Praseodymium(III) complex of 3,6,9-triaza-3,6,9-tris(carboxymethyl)-4-(4-ethoxy-benzyl)-undecanedioic acid,
Cerium(III) complex of 3,6,9-triaza-3,6,9-tris(carboxymethyl)-4-(4-ethoxy-benzyl)-undecanedioic acid,
Lutetium(III) complex of 3,6,9-triaza-3,6,9-tris(carboxymethyl)-4-(4-ethoxy-benzyl)-undecanedioic acid,
Lead (II) complex of 3,6,9-triaza-3,6,9-tris(carboxymethyl)-4-(4-ethoxy-benzyl)-undecanedioic acid,
Bismuth(III) complex of 3,6,9-triaza-3,6,9-tris(carboxymethyl)-4-(4-ethoxy-benzyl)-undecanedioic acid,
Lanthanum(III) complex of 3,6,9-triaza-3,6,9-tris(carboxymethyl)-4-(4-ethoxy-benzyl)-undecanedioic acid,
Dysprosium(III) complex of 3,6,9-triaza-3,6,9-tris(carboxymethyl)-4-(4-ethoxy-benzyl)-undecanedioic acid,
Erbium(III) complex of 3,6,9-triaza-3,6,9-tris(carboxymethyl)-4-(4-ethoxy-benzyl)-undecanedioic acid,
Terbium(III) complex of 3,6,9-triaza-3,6,9-tris(carboxymethyl)-4-(4-ethoxy-benzyl)-undecanedioic acid,
Holmium(III) complex of 3,6,9-triaza-3,6,9-tris(carboxymethyl)-4-(4-ethoxy-benzyl)-undecanedioic acid,
Hafnium(IV) complex of 3,6,9-triaza-3,6,9-tris(carboxymethyl)-4-(4-ethoxy-benzyl)-undecanedioic acid,
Bismuth(III) complex of 3,6,9-triaza-3,6,9-tris(carboxymethyl)-4-(4-ethoxy-benzyl)-undecanedioic acid,
Ytterbium complex of 3,6,9-triaza-3,6,9-tris-(carboxymethyl)-5-{4-[2-(2-ethoxyethoxy)-ethoxy]benzyl}-undecanedioic acid,
Ytterbium complex of 3,6,9-triaza-3,6,9-tris-(carboxymethyl)-4-2-ethoxybenzyl-undecanedioic acid,
Gadolinium(III) complex of 3,6,9-triaza-3,6,9-tris-(carboxymethyl)-4-(4-butyl-benzyl)-undecanedioic acid,
Ytterbium complex of 3,6,9-triaza-3,6,9-tris-(carboxymethyl)-4-(4-butyl-benzyl-undecanedioic acid,
Praseodymium(III) complex of 3,6,9-triaza-3,6,9-tris-(carboxymethyl)-4-(4-butyl-benzyl-undecanedioic acid,
Hafnium(IV) complex of 3,6,9-triaza-3,6,9-tris-(carboxymethyl)-4-(4-butyl-benzyl-undecanedioic acid,
Bismuth(III) complex of 3,6,9-triaza-3,6,9-tris-(carboxymethyl)-4-(4-butyl-benzyl-undecanedioic acid,
Lutetium(III) complex of 3,6,9-triaza-3,6,9-tris-(carboxymethyl)-4-(4-butyl-benzyl-undecanedioic acid,
Lead(II) complex of 3,6,9-triaza-3,6,9-tris-(carboxymethyl)-4-(4-butyl-benzyl-undecanedioic acid,
Bismuth(III) complex of 3,6,9-triaza-3,9-bis-(carboxymethyl)-6-{2-[4-(1,4,7-trioxaoctyl)-phenyl]-1-carboxyethyl}4,8-bis-[4-[1,4,7-trioxaoctyl)-benzyl]-undecanedioic acid,
Ytterbium(III) complex of 3,6,9-triaza-3,6,9-tris-(carboxymethyl)-4,8-bis-(4-ethoxybenzyl)-undecanedioic acid,
Lanthanum(III) complex of 3,6,9-triaza-3,6,9-tris-(carboxymethyl)-4,8-bis-(4-ethoxybenzyl)-undecanedioic acid,
Cerium(III) complex of 3,6,9-triaza-3,6,9-tris-(carboxymethyl)-4,8-bis-(4-ethoxybenzyl)-undecanedioic acid,
Praseodymium(III) complex of 3,6,9-triaza-3,6,9-tris-(carboxymethyl)-4,8-bis-(4-ethoxybenzyl)-undecanedioic acid,
Gadolinium(III) complex of 3,6,9-triaza-3,6,9-tris-(carboxymethyl)-4,8-bis-(4-ethoxybenzyl)-undecanedioic acid,
Terbium(III) complex of 3,6,9-triaza-3,6,9-tris-(carboxymethyl)-4,8-bis-(4-ethoxybenzyl)-undecanedioic acid,
Dysprosium(III) complex of 3,6,9-triaza-3,6,9-tris-(carboxymethyl)-4,8-bis-(4-ethoxybenzyl)-undecanedioic acid,
Holmium(III) complex of 3,6,9-triaza-3,6,9-tris-(carboxymethyl)-4,8-bis-(4-ethoxybenzyl)-undecanedioic acid,
Erbium(III) complex of 3,6,9-triaza-3,6,9-tris-(carboxymethyl)-4,8-bis-(4-ethoxybenzyl)-undecanedioic acid,
Terbium(III) complex of 3,6,9-triaza-3,6,9-tris-(carboxymethyl)-4,8-bis-(4-ethoxybenzyl)-undecanedioic acid,
Lutetium(III) complex of 3,6,9-triaza-3,6,9-tris-(carboxymethyl)-4,8-bis-(4-ethoxybenzyl)-undecanedioic acid,
Hafnium complex of 3,6,9-triaza-3,6,9-tris-(carboxymethyl)-4,8-bis-(4-ethoxybenzyl)-undecanedioic acid,
Tantallum(III) complex of 3,6,9-triaza-3,6,9-tris-(carboxymethyl)-4,8-bis-(4-ethoxybenzyl)-undecanedioic acid,
Lead(II) complex of 3,6,9-triaza-3,6,9-tris-(carboxymethyl)-4,8-bis-(4-ethoxybenzyl)-undecanedioic acid,
Bismuth(III) complex of 3,6,9-triaza-3,6,9-tris-(carboxymethyl)-4,8-bis-(4-ethoxybenzyl)-undecanedioic acid,
Gadolinium complex of 3,6,9-triaza-3,6,9-tris-(carboxymethyl)-2,10-bis-(4-ethoxybenzyl)-undecanedioic acid,
Hafnium complex of 3,6,9-triaza-3,9-bis-(carboxymethyl)-6-{2-[4-carboxymethoxy)-phenyl]-1-carboxyethyl}-4-[-4-propoxybenzyl]-undecanedioic acid, Terbium complex of 3,6,9-triaza-6-(carboxymethyl)-3,9-bis-[2-(4-methoxyphenyl)-1-carboxyethyl]-2,10-bis-(4-methoxybenzyl)-undecanedioic acid, Holmium complex of 3,6,9-triaza-6,9-bis-(carboxymethyl)-3-[(4-methoxybenzyl)-carboxymethyl]-10-(4-ethoxybenzyl)-2-(4-methoxybenzyl)-undecanedioic acid, Erbium complex of 3,6,9-triaza-3,6,9-tris-(carboxymethyl)-2,10-bis-(4-ethoxybenzyl)-4,8-bis-(4-propoxybenzyl)-undecanedioic acid, Dysprosium complex of 3,6,9-triaza-3,6,9-tris-(carboxymethyl)-2-(4-ethoxybenzyl)-undecanedioic acid, Ytterbium complex of 3,6,9-triaza-3,6,9-tris-(carboxymethyl)-2-(benzylmethyl)-undecanedioic acid, as well as their salts and amides.

The mentioned metal complexes are preferably used in the form of their sterile, aqueous solutions. In addition to the metal complexes absorbing the X-rays, the aqueous solution can contain the usual pharmaceutical adjuvants, such as buffers, bases, acids, stabilizers, solubilizers, substances for matching the osmolality and viscosity, pharmacologically effective additives and an excess (about 0.1 to 10 mol % relative to the diagnostically effective metal complex) of free complexing agents or their salts/complexes with weakly bound physiologically compatible ions, such as calcium$^{2+}$, magnesium$^{2+}$ or zinc$^{2+}$ to, for example, improve the elimination of heavy metal ions. Suitable such substances and their ranges of concentration are known to one skilled in the art or can be gathered from the literature.

The metal complexes are used preferably in a concentration of about 0.1 mol–1.0 mol of opacifying metal ion. Higher or lower concentrations are possible depending on the requirements and the solubility of the compound in question. The dosage for the contrast-enhancement in the liver is preferably about 0.1–1.5 mmol/kg of body weight, especially 0.2–0.6 mmol/kg.

The administration can take place in the ways usually employed in medicine. Preferably, the agents are administered by intravenous infusion or injection over a period of about 1 minute to 30 minutes.

In summary, it is to be noted that it has been possible for the first time with the family of substances described herein to achieve a specific contrast medium concentration in the liver in humans, which results in useful diagnostic information with the now available computer-tomographic technology. This finding is all the more surprising as preparations for this purpose have been sought in vain for decades, iodinated X-ray contrast media did not satisfy the requirements despite the presence of all molecular properties theoretically to be required and a substantially higher content of opacifying element in the molecule, the action of the substances according to the invention when used in magnetic resonance imaging occurs at concentrations lower by a factor of 10 than required for X-ray computer tomography; and such lower concentrations are achieved by a great many X-ray contrast media in the liver of humans, without these X-ray contrast media being able to be used for computer tomography, MRI or another opacifying process to improve diagnosis of focal liver changes, findings from animal experiments with respect to suitability of contrast media for contrast enhancement in liver computer tomography thus far have proven completely unreliable.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, are hereby incorporated by reference.

EXAMPLES

The following examples are used for a more detailed explanation of the objects of the invention without intending to be limiting.

Example 1

Dysprosium complex of the disodium salt of 3,6,9-triaza-3,6,9-tris-(carboxymethyl)-2-(4-ethoxybenzyl)-undecanedioic acid a) N-Benzyl-tyrosine-tert-butyl ester 16.9 g (71.5 mmol) of tyrosine-tert-butyl ester and 8.33 g (78.6 mmol) of benzaldehyde are stirred in 50 ml of methanol for 3 hours at 24° C. and then mixed with 3.37 g (53.6 mmol) of sodium cyanoborohydride. After 24 hours of stirring at room temperature, the batch is adjusted to pH 2 by careful addition of semiconcentrated hydrochloric acid, then neutralized with concentrated aqueous sodium bicarbonate solution and, after substantial evaporation of methanol, it is shaken out with ethyl acetate. The organic phase is dried on anhydrous magnesium sulfate, filtered and concentrated by evaporation. The residue is chromatographed on silica gel with diethyl ether/hexane/triethylamine; the product-containing fractions are combined and concentrated by evaporation.

Yield: 15.7 g (67% of theory) of colorless oil. Analysis (relative to solventless substance): Cld: C 73.37, H 7.70, N 4.28, O 14.66 Fnd: C 73.25, H 7.84, N 4.16 b) N-Benzyl-2-(4-hydroxybenzyl)-3-azaglutaric acid-di-tert-butyl ester 15.1 g (46.1 mmol) of N-benzyl-tyrosine-tert-butyl ester (Example a) is dissolved in 50 ml of tetrahydrofuran and mixed with 5 ml of water and 9.54 g (69 mmol) of potassium carbonate. After instillation of 9.89 g (51 mmol) of bromoacetic acid-tert-butyl ester, it is stirred for two days at 65° C. After cooling, it is filtered, concentrated by evaporation in a vacuum and the residue is chromatographed on silica gel with diethyl ether/hexane/triethylamine. The product fractions are concentrated by evaporation in a vacuum and dried.

Yield: 14.9 g (73.3% of theory) of colorless oil.

| Analysis (relative to solventless substance): | | | | |
|---|---|---|---|---|
| Cld: | C 74.33 | H 8.22 | N 3.94 | O 13.50 |
| Fnd: | C 74.27 | H 8.26 | N 3.74 | | c) N-Benzyl-2-(4-ethoxybenzyl)-3-azaglutaric acid-di-tert-butyl ester 13.2 g (30 mmol) of N-benzyl-2-(4-hydroxybenzyl)-3-azaglutaric acid-di-tert-butyl ester (Example b) is dissolved in 50 ml of anhydrous N,N-dimethylformamide and mixed at 0° C. under argon with 1.31 g (33 mmol) of sodium hydride dispersion (60% in mineral oil). The batch is allowed to stir for 15 minutes, then 8.05 g (51.7 mmol) of ethyl iodide is added, the reaction temperature is allowed to increase to room temperature and it is stirred for another three hours. For working-up, the batch is taken up in toluene and shaken out several times against aqueous sodium bicarbonate solution. The organic phase is separated, dried on magnesium sulfate, filtered and concentrated by evaporation. The oily residue is chromatographed for purification on silica gel with hexane/diethyl ether/triethylamine. The product fractions are concentrated by evaporation in a vacuum and dried.

Yield: 12.7 g (90.3% of theory) of colorless oil.

| Analysis (relative to solventless substance): | | | |
|---|---|---|---|
| Cld: | C 71.61 | H 8.37 | N 2.98 | O 17.03 |
| Fnd: | C 71.72 | H 8.43 | N 2.87 | | d) 2-(4-Ethoxybenzyl)-3-azaglutaric acid-di-tert-butyl ester 14.2 g (30.2 mmol) of the compound produced according to Example c) is dissolved in 75 ml of ethanol and, after the addition of 1.4 g of palladium (10%) on activated carbon under hydrogen atmosphere, it is hydrogenated at room temperature until hydrogen absorption is completed. After filtration and concentration by evaporation of the filtrate in a vacuum, a colorless oil is obtained.

Yield: 11.3 g (98.6% of theory)

| Analysis (relative to solventless substance): | | | |
|---|---|---|---|
| Cld: | C 66.46 | H 8.77 | N 3.69 | O 21.08 |
| Fnd: | C 66.44 | H 8.63 | N 3.57 | | e) 3,6-Diaza-3-(tert-butoxycarbonylmethyl)-6-(2-hydroxyethyl)-octanedioic acid-di-tert-butyl ester 20.8 g (200 mmol) of N-(2-hydroxyethyl)-ethylenediamine is reacted with 128.55 g (660 mmol) of bromoacetic acid-tert-butyl ester and 124.4 g (900 mmol) of potassium carbonate in tetrahydrofuran/water analogously to Example b). After chromatographic purification, the title compound is obtained as colorless oil.

Yield: 82.7 g (92.6% of theory)

| Analysis (relative to solventless substance): | | | |
|---|---|---|---|
| Cld: | C 59.17 | H 9.48 | N 6.27 | O 25.08 |
| Fnd: | C 59.24 | H 9.60 | N 6.13 | | f) 3,6-Diaza-3-(tert-butoxycarbonylmethyl)-6-(2-bromoethyl)-octanedioic acid-di-tert-butyl ester A solution of 33.8 g (75.8 mmol) of the compound described in Example e) and 22.9 g (87.1 mmol) of triphenylphosphine in 400 ml of dichloromethane is mixed at 0° C. in portions with 15.5 g (87.1 mmol) of N-bromosuccinimide and then stirred for 20 hours at room temperature. The solution is concentrated by evaporation and the residue is adsorptively precipitated with tert-butyl methyl ether. A precipitate develops, which is separated and washed with tert-butyl methyl ether. The combined filtrates are concentrated by evaporation and the residue is chromatographed on silica gel with hexane/diethyl ether. The concentration by evaporation of the product fractions produces a colorless oil.

Yield: 31.3 g (81.0% of theory)

| Analysis (relative to solventless substance): | | | | |
|---|---|---|---|---|
| Cld: | C 51.87 | H 8.11 | Br 15.68 | N 5.50 | O 18.84 |
| Fnd: | C 51.69 | H 8.20 | Br 15.51 | N 5.43 | | g) 3,6,9-Triaza-3,6,9-tris-(tert-butoxycarbonylmethyl)-2-(4-ethoxybenzyl)-undecanedioic acid-di-tert-butyl ester 7.59 g (20 mmol) of the compound produced according to Example d) and 11.2 g (22 mmol) of 3,6-diaza-3-(tert-butoxycarbonylmethyl)-6-(2-bromoethyl)-octanedioic acid-di-tert-butyl ester (Example f) are introduced into 45 ml of acetonitrile and mixed with 25 ml of 2N phosphate buffer solution (pH 8.0). The batch is stirred vigorously at room temperature for 22 hours, and the aqueous phosphate buffer phase is exchanged after 2 and 7 hours for fresh buffer solution. Then, the organic phase is concentrated by evaporation in a vacuum, and the residue is chromatographed on silica gel with hexane/ethyl acetate/triethylamine. The product-containing fractions are concentrated by evaporation in a vacuum.

Yield: 13.3 g (82.3% of theory) of colorless oil.

| Analysis (relative to solventless substance): | | | |
|---|---|---|---|
| Cld: | C 63.92 | H 9.11 | N 5.20 | O 21.78 |
| Fnd: | C 64.07 | H 9.20 | N 5.08 | | h) 3,6,9-Triaza-3,6,9-tris-(carboxymethyl)-2-(4-ethoxybenzyl)-undecanedioic acid 12.6 g (15.6 mmol) of the pentaester described in Example g) is dissolved in 50 ml of methanol and mixed with 40 ml of 2N sodium hydroxide solution. It is refluxed for three hours, the methanol is drawn off in a vacuum and stirred for another two hours at 60° C. Then, it is adjusted to pH 1 with concentrated hydrochloric acid, evaporated to dryness in a vacuum and the residue is adsorptively precipitated with isopropanol. After filtration and concentration by evaporation of the filtrate in a vacuum, a colorless solid is obtained.

Yield: 7.5 g (91.1% of theory)

| Analysis (relative to anhydrous substance): | | | |
|---|---|---|---|
| Cld: | C 52.37 | H 6.31 | N 7.97 | O 33.36 |
| Fnd: | C 52.24 | H 6.45 | N 7.81 | | i) Dysprosium complex of disodium salt of 3,6,9-triaza-3,6,9-tris-(carboxymethyl)-2-(4-ethoxybenzyl)-undecanedioic acid 6.9 g (13 mmol) of the penta acid described in Example h) is taken up in 30 ml of water, mixed with 2.42 g (6.5 mmol) of dysprosium oxide and stirred for eight hours at 85° C. Then, it is adjusted to pH 7.2 with diluted sodium hydroxide solution, filtered and the filtrate is freeze-dried.

Yield: 8.45 g (88.9% of theory) of colorless lyophilizate.

| Analysis (relative to solventless substance): | | | | | |
|---|---|---|---|---|---|
| Cld: | C 37.79 | H 3.86 | Dy 22.23 | N 5.75 | Na 6.29 | O 24.08 |
| Fnd: | C 37.64 | H 3.97 | Dy 22.12 | N 5.62 | Na 6.04 | |

Example 2

Ytterbium complex of the disodium salt of 3,6,9-triaza-3,6,9-tris-(carboxymethyl)-2-(benzylmethyl)-undecanedioic acid a) 3,6,9-Triaza-2-(benzylmethyl)-nonanoic acid benzyl ester 13.4 g (50.0 mmol) of 2-oxo-4-phenylbutyric acid benzyl ester and 31.0 g (300 mmol) of diethylenetriamine are stirred in 200 ml of methanol for two hours at room temperature. Then, 0.95 g (25.0 mmol) of sodium borohydride is added in portions at 0° C. It is allowed to stir overnight, and the reaction mixture is gently concentrated by evaporation in a vacuum. The residue is dispersed between dichloromethane and water, the organic phase is dried on sodium sulfate, filtered and concentrated by evaporation. The residue is chromatographed on silica gel with use of dichloromethane/methanol/triethylamine (70:30:1) as mobile solvent. The fractions that contain the pure product are combined and concentrated by evaporation.

Yield: 13.5 g (75.9% of theory) of pale yellow oil.

| Analysis (relative to solventless substance): | | | | |
|---|---|---|---|---|
| Cld: | C 70.96 | H 8.22 | N 11.82 | O 9.00 |
| Fnd: | C 70.88 | H 8.41 | N 12.04 | | b) 3,6,9-Triaza-3,6,9-tris-(tert-butoxycarbonylmethyl)-2-(benzylmethyl)-undecanedioic acid-di-tert-butyl ester 6.91 g (50.0 mmol) of potassium carbonate is dissolved in 7 ml of water and mixed at 35° C. with 3.55 g (10.0 mmol) of triamine from Example a) in 50 ml of tetrahydrofuran. 9.75 g (50.0 mmol) of bromoacetic acid-tert-butyl ester is added drop by drop and the batch is stirred for three hours at 60° C. After 15 hours of stirring at room temperature, the reaction mixture is mixed with a little water and shaken out with ethyl acetate. The organic phase is dried on sodium sulfate, concentrated by evaporation, and the residue is chromatographed on silica gel (ethyl acetate/acetone). After the concentration by evaporation of the product-containing fractions, the pentaester is obtained as colorless oil.

Yield: 6.64 g (81.8% of theory)

| Analysis (relative to solventless substance): | | | | |
|---|---|---|---|---|
| Cld: | C 66.56 | H 8.56 | N 5.18 | O 19.70 |
| Fnd: | C 66.79 | H 8.32 | N 4.93 | | c) Ytterbium complex of the disodium salt of 3,6,9-triaza-3,6,9-tris-(carboxymethyl)-2-(benzylmethyl)-undecanedioic acid 15.6 g (19.2 mmol) of pentaester (from 3 batches corresponding to Example b)) is dissolved in 80 ml of methanol and reacted with 76.8 ml of 2N sodium hydroxide solution. It is stirred for five hours at 55° C., then the methanol is evaporated, water is added and it is evaporated again. It is taken up in water and adjusted to pH 1.9 with acid ion exchanger. After the exchanger is filtered out, the aqueous solution is mixed with 3.79 g (9.61 mmol) of ytterbium oxide and stirred at 95° C. After the complexing is completed, it is filtered, adjusted to pH 7.2, stirred with 0.2 g of activated carbon for ten minutes at 90° C., filtered again and the filtrate is freeze-dried.

Yield: 12.8 g (93.8% of theory) of colorless lyophilizate.

| Analysis (relative to anhydrous substance): | | | | | |
|---|---|---|---|---|---|
| Cld: | C 37.14 | H 4.28 | N 5.58 | O 23.35 | Yb 20.86 Na 6.10 |
| Fnd: | C 37.22 | H 4.40 | N 5.62 | | Yb 20.75 Na 6.03 |

Example 3

Bismuth complex of the disodium salt of 3,6,9-triaza-3,9-bis-(carboxymethyl)-6-{2-[4-(1,4,7-trioxaoctyl)-phenyl]-1-carboxyethyl}-4,8-bis-[4-(1,4,7-trioxaoctyl)-benzyl]-undecanedioic acid a) N-Benzyloxycarbonyl-3-[4-(1,4,7-trioxaoctyl)-phenyl]-alanine-methyl ester 6.59 g (20 mmol) of N-benzyloxycarbonyl-tyrosinemethyl ester is dissolved in 25 ml of anhydrous N,N-di-methylformamide and mixed at 0° C. under argon with 0.81 g (20.5 mmol) of sodium hydride dispersion (60% in mineral oil). The batch is allowed to stir for 10 minutes, then 3.75 g (20.5 mmol) of 1-bromo-2-(2-methoxyethoxy)-ethane is added, the reaction temperature is allowed to increase to room temperature and stirred for another three hours. For working-up, the batch is taken up in toluene and shaken out several times against aqueous sodium bicarbonate solution. The organic phase is separated, dried on magnesium sulfate, filtered and concentrated by evaporation. The oily residue is chromatographed for purification on silica gel with hexane/diethyl ether/triethylamine.

Yield: 7.6 g (88% of theory) of colorless oil.

| Analysis (relative to solventless substance): | | | | |
|---|---|---|---|---|
| Cld: | C 64.02 | H 6.77 | N 3.25 | O 25.96 |
| Fnd: | C 64.13 | H 6.59 | N 3.11 | | b) N-Benzyloxycarbonyl-2-amino-2-[4-(1,4,7-trioxaoctyl)benzyl]-ethanol 7.35 g (17 mmol) of N-benzyloxycarbonyl-3-[4-(1,4,7-trioxaoctyl)-phenyl]-alanine-methyl ester (Example a) is dissolved in 35 ml of tert-butyl methyl ether and mixed with 0.9 g (23.8 mmol) of sodium borohydride. At 5° C., 10 ml of methanol is added, and it is stirred for four hours under argon at constant temperature. Then, 1.5 ml of acetic acid, dissolved in 5 ml of tetrahydrofuran, is added, mixed with 5 ml of water and stirred for ten minutes at room temperature. The organic phase is separated, washed with water and dried on sodium sulfate. The drying agent is suctioned off, the filtrate is concentrated by evaporation and the residue is chromatographed for purification on silica gel.

Yield: 6.4 g (93.3% of theory)

| Analysis (relative to solventless substance): | | | | |
|---|---|---|---|---|
| Cld: | C 65.49 | H 7.24 | N 3.47 | O 23.79 |
| Fnd: | C 65.34 | H 7.32 | N 3.36 | | c) 2-Amino-2-[4-(1,4,7-trioxaoctyl)-benzyl]-ethanol 6.3 g (15.6 mmol) of the compound produced according to Example b) is dissolved in 35 ml of ethanol and after the addition of 0.6 g of palladium (10%) on activated carbon, it is hydrogenated under hydrogen atmosphere at room temperature until hydrogen absorption is completed. After filtration and concentration by evaporation of the filtrate in a vacuum, a colorless oil is obtained.

Yield: 4.1 g (97.6% of theory)

| Analysis (relative to solventless substance): | | | | |
|---|---|---|---|---|
| Cld: | C 62.43 | H 8.61 | N 5.20 | O 23.76 |
| Fnd: | C 62.26 | H 8.67 | N 5.04 | | d) N-{2-Hydroxy-1-[4-(1,4,7-trioxaoctyl)-benzyl]-ethyl}-iminodiacetic acid-di-tert-butyl ester 3.9 g (14.5 mmol) of the compound described in Example c), 6.2 g (32 mmol) of bromoacetic acid-tert-butyl ester and 4.4 g (32 mmol) of potassium carbonate are stirred in 15 ml of tetrahydrofuran/water (2:1) for two days at 65° C. After cooling, it is filtered, concentrated by evaporation in a vacuum, and the residue is chromatographed on silica gel with diethyl ether/hexane/triethylamine. The product fractions are concentrated by evaporation in a vacuum and dried.

Yield: 6.1 g (84.5% of theory)

| Analysis (relative to solventless substance): | | | | |
|---|---|---|---|---|
| Cld: | C 62.76 | H 8.71 | N 2.82 | O 25.72 |
| Fnd: | C 62.59 | H 8.88 | N 2.80 | | e) N-{2-Bromo-1-[4-(1,4,7-trioxaoctyl)-benzyl]-ethyl}-iminodiacetic acid-di-tert-butyl ester A solution of 5.8 g (11.6 mmol) of the compound described in Example d) and 3.35 g (12.8 mmol) of triphenylphosphine in 50 ml of dichloromethane is mixed at 0° C. in portions with 2.28 g (12.8 mmol) of N-bromosuccinimide and then stirred for 20 hours at room temperature. The solution is concentrated by evaporation and the residue is absorptively precipitated with tert-butyl methyl ether. A precipitate develops, which is separated and washed with tert-butyl methyl ether. The combined filtrates are concentrated by evaporation and the residue is chromatographed on silica gel with hexane/diethyl ether. The concentration by evaporation of the product fractions yields a colorless oil.

Yield: 5.9 g (90.7% of theory)

| Analysis (relative to solventless substance): | | | | | |
|---|---|---|---|---|---|
| Cld: | C 55.71 | H 7.55 | Br 14.26 | N 2.50 | O 19.98 |
| Fnd: | C 55.62 | H 7.39 | Br 14.14 | N 2.38 | | f) N-Benzyloxycarbonyl-3-[4-(1,4,7-trioxaoctyl)-phenyl]-alanine-tert-butyl ester 7.43 g (20 mmol) of N-benzyloxycarbonyl-tyrosine-tert-butyl ester is reacted with 1-bromo-2-(2-methoxyethoxy) ethane to alkylated phenol analogously to Example a).

Yield: 8.2 g (86.6% of theory) of colorless oil.

| Analysis (relative to solventless substance): | | | | |
|---|---|---|---|---|
| Cld: | C 65.94 | H 7.45 | N 2.96 | O 23.65 |
| Fnd: | C 65.98 | H 7.52 | N 2.78 | | g) 3-[4-(1,4,7-Trioxaoctyl)-phenyl]-alanine-tert-butyl ester
7.9 g (16.7 mmol) of the compound produced according to Example f) is dissolved in 40 ml of ethanol and after the addition of 0.8 g of palladium (10%) on activated carbon, it is hydrogenated under hydrogen atmosphere at room temperature until hydrogen absorption is completed. After filtration and concentration by evaporation of the filtrate in a vacuum, a colorless oil is obtained.

Yield: 5.5 g (97.0% of theory)

| Analysis (relative to solventless substance): | | | | |
|---|---|---|---|---|
| Cld: | C 63.69 | H 8.61 | N 4.13 | O 23.57 |
| Fnd: | C 63.57 | H 8.71 | N 4.05 | | h) 3,6,9-Triaza-3,9-bis-(tert-butoxycarbonylmethyl)-6-{2-[4-(1,4,7-trioxaoctyl)-phenyl]-1-tert-butoxycarbonylethyl}-4,8-bis-[4-(1,4,7-trioxaoctyl)-benzyl]-undecanedioic acid-di-tert-butyl ester 5.2 g (15.3 mmol) of the amine produced according to Example g) and 18.9 g (33.7 mmol) of the bromide produced according to Example e) is introduced into 65 ml of acetonitrile and mixed with 30 ml of 2N phosphate buffer solution (pH 8.0). The batch is vigorously stirred at room temperature for 30 hours, and the aqueous phosphate buffer phase is exchanged for fresh buffer solution after 2, 8 and 18 hours. Then, the organic phase is concentrated by evaporation in a vacuum, and the residue is chromatographed on silica gel with hexane/ethyl acetate/triethylamine. The product-containing fractions are concentrated by evaporation in a vacuum.

Yield: 16.3 g (82.0% of theory) of colorless oil.

| Analysis (relative to solventless substance): | | | | |
|---|---|---|---|---|
| Cld: | C 64.74 | H 8.62 | N 3.24 | O 23.41 |
| Fnd: | C 64.58 | H 8.70 | N 3.29 | | i) Bismuth complex of the disodium salt of 3,6,9-triaza-3,9-bis-(carboxymethyl)-6-{2-[4-(1,4,7-trioxaoctyl)phenyl]-1-carboxyethyl}-4,8-bis-[4-(1,4,7-trioxaoctyl)benzyl]-undecanedioic acid 15.9 g (12.2 mmol) of the compound produced according to Example h) is dissolved in 65 ml of tetrahydrofuran and mixed with 75 ml of 2N sodium hydroxide solution, it is stirred for four hours at 55° C., adjusted to pH 1.3 with concentrated hydrochloric acid, greatly concentrated by evaporation in a rotary evaporator and the residue is purified by ion exchange chromatography (cationic exchanger (H$^+$ form), eluent: ammonia-water solution). The eluate is concentrated by evaporation and greatly dried under high vacuum, by which the free complexing agent is obtained.

The penta acid is taken up in 250 ml of water and mixed with 6.22 g (12.2 mmol) of bismuth oxycarbonate. The suspension is stirred for 25 hours at 100° C. and filtered. Then, it is adjusted to pH 7.2 with 1N sodium hydroxide solution. Then, after the addition of 1.6 g of activated carbon, the solution is stirred for one hour at 60° C. and filtered. After freeze-drying, the filtrate yields a colorless solid.

Yield: 14.7 g (95% of theory)

| Analysis (relative to anhydrous substance): | | | | | | |
|---|---|---|---|---|---|---|
| Cld: | C 47.36 | H 5.25 | N 3.31 | O 23.97 | Bi 16.48 | Na 3.63 |
| Fnd: | C 47.21 | H 5.44 | N 3.26 | | Bi 16.27 | Na 3.29 |

Example 4

Ytterbium complex of the disodium salt of 3,6,9-triaza-3,6,9-tris-(carboxymethyl)-4,8-bis-(4-ethoxybenzyl)-undecanedioic acid a) 2-(4-Ethoxybenzyl)-2-aminoethanol
45.0 g (136.7 mmol) of [2-(4-ethoxyphenyl)-1-hydroxyphenyl)-ethyl]-carbaminic acid benzyl ester (DE 4302287 A1), dissolved in 300 ml of ethanol, is mixed with 3.0 g of palladium (10%) on activated carbon and it is hydrogenated until hydrogen absorption is completed. Then, catalyst is filtered out, and the filtrate is evaporated to dryness.

Yield: 26.7 g (100% of theory) of colorless solid.

| Analysis (relative to solventless substance): | | | | |
|---|---|---|---|---|
| Cld: | C 69.28 | H 7.04 | N 4.25 | O 19.43 |
| Fnd: | C 69.25 | H 7.11 | N 4.13 | | b) N,N-[1-(4-Ethoxybenzyl)-2-hydroxyethyl]-iminodiacetic acid-di-tert-butyl ester 20 g (102.4 mmol) of 2-(4-ethoxybenzyl)-2-aminoethanol (Example a) is reacted with 40 g (205 mmol) of bromoacetic acid-tert-butyl ester analogously to Example 3d). After chromatographic purification, the dialkylation product is obtained as colorless oil.

Yield: 37.6 g (86.7% of theory)

| Analysis (relative to solventless substance): | | | | |
|---|---|---|---|---|
| Cld: | C 65.22 | H 8.81 | N 3.31 | O 22.66 |
| Fnd: | C 65.07 | H 8.92 | N 3.28 | | c) N,N-[2-Bromo-1-(4-ethoxybenzyl)-ethyl]-iminodiacetic acid-di-tert-butyl ester By reaction of 9.3 g (21.9 mmol) of the diester of Example b) with triphenylphosphine and N-bromosuccinimide analogously to Example 3e), the bromide is obtained as pale yellow oil.

Yield: 8.9 g (83.5% of theory)

| Analysis (relative to solventless substance): | | | | |
|---|---|---|---|---|
| Cld: | C 56.79 | H 7.46 | Br 16.43 | N 2.88 | O 16.44 |
| Fnd: | C 56.63 | H 7.50 | Br 16.29 | N 2.69 | | d) 3,6,9-Triaza-3,6,9-tris-(tert-butoxycarbonylmethyl)-4,8-bis-(4-ethoxybenzyl)-undecanedioic acid-di-tert-butyl ester 1.4 g (8.5 mmol) of glycine-tert-butyl ester hydrochloride and 8.5 g (17.5 mmol) of the bromide produced according to Example c) are introduced into 45 ml of acetonitrile and mixed with 20 ml of 2N phosphate buffer solution (pH 8.0). The batch is vigorously stirred at room temperature for 28 hours, and the aqueous phosphate buffer phase is exchanged for fresh buffer solution after 2, 8 and 16 hours. Then, the organic phase is concentrated by evaporation in a vacuum and the residue is chromatographed on silica gel. The product-containing fractions are concentrated by evaporation in a vacuum.

Yield: 5.3 g (66.2% of theory) of colorless oil.

| Analysis (relative to solventless substance): | | | | |
|---|---|---|---|---|
| Cld: | C 66.29 | H 8.88 | N 4.46 | O 20.38 |
| Fnd: | C 66.37 | H 8.79 | N 4.33 | | e) Ytterbium complex of the disodium salt of 3,6,9-triaza-3,6,9-tris-(carboxymethyl)-4,8-bis-(4-ethoxybenzyl) undecanedioic acid 4.7 g (5 mmol) of the penta-tert-butyl ester (Example d) is dissolved in 25 ml of tetrahydrofuran and mixed with 20 ml of 2N sodium hydroxide solution, it is stirred for two hours at 50° C., adjusted to pH 1 with concentrated hydrochloric acid, greatly concentrated by evaporation in a rotary evaporator and the residue is purified by ion exchange chromatography (cationic exchanger ($H^+$ form), eluent: ammonia-water solution). The eluate is concentrated by evaporation and dried under high vacuum, by which the free ligand is obtained.

The penta acid is taken up in 100 ml of water and mixed with 1.31 g (2.5 mmol) of ytterbium carbonate. The suspension is stirred for two hours at 60° C. and filtered. Then, it is adjusted to pH 7.2 with 1N sodium hydroxide solution. Then, after the addition of 0.5 g of activated carbon, the solution is stirred at 50° C. for one hour and filtered. After freeze-drying, the filtrate yields a colorless solid.

Yield: 4.1 g (94% of theory)

| Analysis (relative to anhydrous substance): | | | | | | |
|---|---|---|---|---|---|---|
| Cld: | C 43.89 | H 4.37 | N 4.80 | O 21.92 | Yb 19.76 | Na 5.26 |
| Fnd: | C 43.71 | H 4.47 | N 4.63 | | Yb 19.58 | Na 4.96 |

Example 5

Gadolinium complex of the disodium salt of 3,6,9-triaza-3,6,9-tris-(carboxymethyl)-2,10-bis-(4-ethoxybenzyl)-undecanedioic acid a) 3,6,9-Triaza-2,10-bis-(4-ethoxybenzyl)-undecanedioic acid-diisopropyl ester, trihydrochloride 10.4 g (50 mmol) of α-oxo-4-ethoxyphenylacetic acid (Bandyopahyay et al., J. Ind. Chem. Soc. 66(4), 239, 1989) is dissolved in 55 ml of methanol and reacted with 2.58 g (25 mmol) of diethylenetriamine. After six hours at 60° C., it is allowed to cool to room temperature and 0.76 g (20 mmol) of sodium borohydride is added. It is allowed to stir overnight and then the reaction mixture is mixed carefully with diluted hydrochloric acid until no more gas generation can be observed. The reaction mixture is concentrated by evaporation and dried in an oil pump vacuum for several hours at 100° C. The residue is taken up in isopropanol. Hydrogen chloride gas is introduced until saturation is achieved, stirred for two hours at room temperature and then for eight hours at 85° C. Then, it is concentrated by evaporation, the residue is dispersed between ethyl acetate and sodium bicarbonate solution, the organic phase is dried on sodium sulfate, filtered and concentrated by evaporation. In the solution of the residue in tert-butyl methyl ether, hydrogen chloride gas is introduced until saturation is achieved, and the settled precipitate is suctioned off.

Yield: 13.7 g (80.4% of theory) of pale yellow solid.

| Analysis (relative to solventless substance): | | | | | |
|---|---|---|---|---|---|
| Cld: | C 56.43 | H 7.70 | Cl 15.62 | N 6.17 | O 14.09 |
| Fnd: | C 56.51 | H 7.61 | Cl 15.29 | N 6.30 | | b) 3,6,9-Triaza-3,6,9-tris-(tert-butoxycarbonylmethyl)-2,10-bis-(4-ethoxybenzyl)-undecanedioic acid-diisopropyl ester 13.3 g (19.5 mmol) of diester of Example a) is reacted with 12.57 g (64.4 mmol) of bromoacetic acid-tert-butyl ester analogously to Example 3d).

After chromatographic purification, the title compound is obtained as colorless oil.

Yield: 14.6 g (81.9% of theory)

| Analysis (relative to solventless substance): | | | | |
|---|---|---|---|---|
| Cld: | C 65.69 | H 8.71 | N 4.60 | O 21.00 |
| Fnd: | C 65.53 | H 8.84 | N 4.50 | | c) Gadolinium complex of the disodium salt of 3,6,9-triaza-3,6,9-tris-(carboxymethyl)-2,10-bis-(4-ethoxybenzyl) undecanedioic acid 14.2 g (15.5 mmol) of the compound produced according to Example b) is dissolved in 45 ml of tetrahydrofuran and mixed with 55 ml of 2N sodium hydroxide solution, it is stirred for three hours at 55° C., adjusted to pH 1 with concentrated hydrochloric acid, greatly concentrated by evaporation in a rotary evaporator and the residue is purified by ion exchange chromatography (cationic exchanger (H$^+$ form), eluent: ammonia-water solution). The eluate is concentrated by evaporation and greatly dried under high vacuum, by which the free complexing agent is obtained. The penta acid is taken up in 120 ml of water and mixed with 2.81 g (7.77 mmol) of gadolinium oxide. The suspension is stirred for 7 hours at 90° C. and filtered. Then, it is adjusted to pH 7.1 with 1N sodium hydroxide solution. Then, after the addition of 1.4 g of activated carbon, the solution is stirred at 70° C. for one hour and filtered. The filtrate is freeze-dried.

Yield: 12.4 g (93% of theory) of colorless solid.

| Analysis (relative to anhydrous substance): | | | | | | |
|---|---|---|---|---|---|---|
| Cld: | C 44.70 | H 4.45 | N 4.89 | O 22.33 | Gd 18.29 | Na 5.35 |
| Fnd: | C 44.56 | H 4.52 | N 4.81 | | Gd 18.14 | Na 5.09 |

Example 6

Hafnium complex of the disodium salt of 3,6,9-triaza-3,9-bis-(carboxymethyl)-6-{2-[4-(carboxymethoxy)-phenyl]-1-carboxyethyl}-4-[4-propoxybenzyl]-undecanedioic acid a) N-Benzyloxycarbonyl-3-[4-propoxyphenyl]-alanine-methyl ester 4.94 g (15 mmol) of N-benzyloxycarbonyl-tyrosinemethyl ester is dissolved in 25 ml of anhydrous N,N-dimethylformamide and mixed at 5° C. under argon with 0.61 g (15.5 mmol) of sodium hydride dispersion (60% in mineral oil). The batch is allowed to stir for 10 minutes, then 1.91 g (15.5 mmol) of propyl bromide is added, the reaction temperature is allowed to increase to room temperature and it is stirred for another two hours. For working-up, the batch is taken up in ethyl acetate and shaken out several times against aqueous sodium bicarbonate solution. The organic phase is separated, dried on magnesium sulfate, filtered and concentrated by evaporation. The residue is chromatographed for purification on silica gel with hexane/diethyl ether/triethylamine.

Yield: 4.3 g (74.7% of theory) of colorless oil.

| Analysis (relative to solventless substance): | | | | |
|---|---|---|---|---|
| Cld: | C 67.91 | H 6.78 | N 3.77 | O 21.54 |
| Fnd: | C 67.78 | H 6.64 | N 3.83 | | b) N-Benzyloxycarbonyl-2-amino-2-[4-propoxybenzyl]-ethanol 4.15 g (11.2 mmol) of N-benzyloxycarbonyl-3-[4-propoxyphenyl]-alanine-methyl ester is dissolved in 20 ml of tert-butyl methyl ether and mixed with 0.17 g (4.5 mmol) of sodium borohydride. At 0° C., 6 ml of methanol is added and it is stirred for three hours under argon at a temperature below 5° C. Then, 0.8 ml of acetic acid, dissolved in 3 ml of tetrahydrofuran, is added, mixed with 3 ml of water and stirred for ten minutes at room temperature. The organic phase is separated, washed with water and dried on sodium sulfate. The drying agent is suctioned off, the filtrate is concentrated by evaporation and the residue is chromatographed for purification on silica gel (eluent: ethyl acetate/hexane).

Yield: 3.55 g (92.3% of theory)

| Analysis (relative to solventless substance): | | | | |
|---|---|---|---|---|
| Cld: | C 69.95 | H 7.34 | N 4.08 | O 18.64 |
| Fnd: | C 69.74 | H 7.42 | N 3.96 | | c) 2-Amino-2-[4-propoxybenzyl]-ethanol 3.4 g (10 mmol) of the Z-protected amine of Example b) is hydrogenated under palladium catalysis analogously to Example 3c).

Yield: 2.0 g (96.5% of theory) of colorless oil.

| Analysis (relative to solventless substance): | | | | |
|---|---|---|---|---|
| Cld: | C 68.87 | H 9.15 | N 6.69 | O 15.29 |
| Fnd: | C 69.02 | H 9.08 | N 6.47 | | d) N-[1-(4-Propoxybenzyl)-2-hydroxyethyl]-iminodiacetic acid-di-tert-butyl ester 1.9 g (9.1 mmol) of the amine of Example c) is reacted with 3.9 g (20 mmol) of bromoacetic acid-tert-butyl ester analogously to Example 3d). After chromatographic purification on silica gel, the dialkylation product is obtained as colorless oil.

Yield: 3.6 g (90.4% of theory)

| Analysis (relative to solventless substance): | | | | |
|---|---|---|---|---|
| Cld: | C 65.88 | H 8.98 | N 3.20 | O 21.94 |
| Fnd: | C 65.97 | H 9.06 | N 3.14 | | e) N-[2-Bromo-1-(4-propoxybenzyl)-ethyl]-iminodiacetic acid-di-tert-butyl ester

From 3.4 g (7.77 mmol) of the diester of Example d) and triphenylphosphine and N-bromosuccinimide, the bromide is obtained as yellow oil analogously to Example 3e).

Yield: 3.25 g (83.6% of theory)

| Analysis (relative to solventless substance): | | | | | |
|---|---|---|---|---|---|
| Cld: | C 56.60 | H 7.65 | Br 15.97 | N 2.80 | O 15.98 |
| Fnd: | C 56.51 | H 7.47 | Br 16.04 | N 2.64 | | f) N-Benzyloxycarbonyl-3-[4-(tert-butoxycarbonylmethoxy)phenyl]-alanine-tert-butyl ester 5.57 g (15 mmol) of N-benzyloxycarbonyl-tyrosine-tert-butyl ester is reacted with bromoacetic acid-tert-butyl ester to alkylated phenol analogously to Example 3a).

Yield: 6.1 g (83.7% of theory) of colorless oil.

| Analysis (relative to solventless substance): | | | | |
|---|---|---|---|---|
| Cld: | C 66.79 | H 7.26 | N 2.88 | O 23.06 |
| Fnd: | C 66.62 | H 7.17 | N 2.81 | | g) N-[N',N'-Bis-(tert-butoxycarbonylmethyl)-2-aminoethyl]-N-benzyloxycarbonyl-3-[4-(tert-butoxycarbonylmethoxy)phenyl]-alanine-tert-butyl ester 5.9 g (12.1 mmol) of the amine of Example f) is mixed in 20 ml of N,N-dimethylformamide at 0° C. with 0.56 g (14.0 mmol) of sodium hydride. After 15 minutes, 4.69 g (13.3 mmol) of N,N-bis-[(tert-butoxycarbonyl)-methyl]-2-bromoethylamine (M. Williams and H. Rapoport, J. Org. Chem. 58, 1151 (1993)) is added and stirring of the batch is allowed to continue overnight at room temperature. Then, the organic phase is shaken out with tert-butyl methyl ether/sodium bicarbonate solution, the tert-butyl methyl ether phase is dried on sodium sulfate and filtered. Then, the organic phase is concentrated by evaporation in a vacuum, and the residue is chromatographed on silica gel with hexane/ethyl acetate/triethylamine. The product-containing fractions are concentrated by evaporation in a vacuum.

Yield: 6.9 g (75.3% of theory) of yellowish oil.

| Analysis (relative to solventless substance): | | | | |
|---|---|---|---|---|
| Cld: | C 65.06 | H 7.99 | N 3.70 | O 23.25 |
| Fnd: | C 65.20 | H 8.14 | N 3.53 | | h) N-[N',N'-Bis-(tert-butoxycarbonylmethyl)-2-aminoethyl]-3-[4-(tert-butoxycarbonylmethoxy)-phenyl]-alanine-tert-butyl ester 6.75 g (8.9 mmol) of the benzyloxycarbonyl-protected amine (Example g) is hydrogenated with the addition of 0.7 g of palladium (10%) on activated carbon at normal pressure and room temperature. After hydrogen absorption is completed, the catalyst is filtered out and the filtrate is evaporated to dryness.

Yield: 5.5 g (99.2% of theory) of colorless oil.

| Analysis (relative to solventless substance): | | | | |
|---|---|---|---|---|
| Cld: | C 63.64 | H 8.74 | N 4.50 | O 23.12 |
| Fnd: | C 63.49 | H 8.87 | N 4.63 | | i) 3,6,9-Triaza-3,9-bis-(tert-butoxycarbonylmethyl)-6-{2-[4-(tert-butoxycarbonylmethoxy)-phenyl]-1-(tert-butoxycarbonyl)-ethyl}-4-[4-propoxybenzyl]-undecanedioic acid-di-tert-butyl ester 5.2 g (8.3 mmol) of the amine produced according to Example h) and 4.36 g (8.7 mmol) of the bromide obtained according to Example e) are dissolved in 35 ml of acetonitrile and mixed with 15 ml of 2N phosphate buffer solution (pH 8.0). The batch is vigorously stirred at room temperature for 36 hours, and the aqueous phosphate buffer phase is exchanged for fresh buffer solution after 2, 8 and 24 hours. Then, the organic phase is concentrated by evaporation in a vacuum and the residue is chromatographed on silica gel with hexane/diethyl ether/triethylamine. The product-containing fractions are concentrated by evaporation in a vacuum.

Yield: 7.6 g (87.8% of theory) of yellowish oil.

| Analysis (relative to solventless substance): | | | | |
|---|---|---|---|---|
| Cld: | C 65.68 | H 8.80 | N 4.03 | O 21.49 |
| Fnd: | C 65.54 | H 8.91 | N 3.89 | | j) 3,6,9-Triaza-3,9-bis-(carboxymethyl)-6-{2-[4-(carboxymethoxy)-phenyl]-1-carboxyethyl}-4-[4-propoxybenzyl]-undecanedioic acid 7.3 g (7 mmol) of the hexaester of Example i) is dissolved in 35 ml of methanol and stirred with 20 ml of 2N sodium hydroxide solution at 70° C. for five hours. Then, the methanol is distilled off, taken up in water and precipitated with concentrated hydrochloric acid. The solid is suctioned off, washed neutral with water and the ligands are dried at 50° C. in a vacuum.

Yield: 4.36 g (88.3% of theory) of colorless solid.

| Analysis (relative to solventless substance): | | | | |
|---|---|---|---|---|
| Cld: | C 56.17 | H 6.14 | N 5.95 | O 31.74 |
| Fnd: | C 56.03 | H 6.01 | N 6.13 | | k) Hafnium complex of the disodium salt of 3,6,9-triaza-3,9-bis-(carboxymethyl)-6-{2-[4-(carboxymethoxy)-phenyl]-1-carboxyethyl}-4-[4-propoxybenzyl]-undecanedioic acid 4.2 g (6 mmol) of hexa acid of Example j) is suspended in 120 ml of water and mixed with 1.47 g (6 mmol) of hafnium hydroxide (D. J. Williams et al., J. Chem. Soc. Dalton Trans. 2475, 1992). The reaction solution is stirred for 36 hours at 100° C. After complexing is completed, it is filtered, concentrated by evaporation to about half the prior volume, and freeze-dried.

Yield: 5.1 g (92% of theory) of colorless lyophilizate.

| Analysis (relative to anhydrous substance): | | | | | | |
|---|---|---|---|---|---|---|
| Cld: | C 42.89 | H 4.04 | N 4.55 | O 24.24 | Hf 19.31 | Na 4.98 |
| Fnd: | C 42.76 | H 4.20 | N 4.41 | | Hf 19.13 | Na 4.72 |

Example 7

Terbium complex of the disodium salt of 3,6,9-triaza-6-(carboxymethyl)-3,9-bis-[2-(4-methoxyphenyl)-1-carboxyethyl]-2,10-bis-(4-methoxybenzyl)-undecanedioic acid a) 3-[4-Methoxyphenyl]-alanine-tert-butyl ester 7.12 g (30 mmol) of tyrosine-tert-butyl ester is dissolved in 28 ml of anhydrous N,N-dimethylformamide and mixed at 50° C. under argon with 1.21 g (31 mmol) of sodium hydride dispersion (60% in mineral oil). The batch is allowed to stir for 15 minutes, then 4.4 g (31 mmol) of methyl iodide is added, the reaction temperature is allowed to increase to room temperature and it is stirred for another hour. For working-up, the batch is taken up in ethyl acetate and shaken out several times against aqueous sodium bicarbonate solution. The organic phase is separated, dried on magnesium sulfate, filtered and concentrated by evaporation. The residue is chromatographed for purification on silica gel with hexane/diethyl ether/ triethylamine.

Yield: 6.8 g (90.2% of theory) of colorless oil.

Analysis (relative to solventless substance):

| Cld: | C 66.91 | H 8.42 | N 5.57 | O 19.10 |
|------|---------|--------|--------|---------|
| Fnd: | C 66.98 | H 8.55 | N 5.33 |         | b) 3-[4-Methoxyphenyl]-2-bromo-propionicacid-tert-butyl ester 6.55 g (26.1 mmol) of the amino acid ester of Example a) is converted to the corresponding bromide analogously to the method of A. Spaltenstein, et al. (THL 34, p. 1457, 1993). After chromatographic purification on silica gel, the product is obtained as pale yellow solid.

Yield: 6.4 g (77.8% of theory)

Analysis (relative to solventless substance):

| Cld: | C 53.35 | H 6.08 | Br 25.35 | O 15.23 |
|------|---------|--------|----------|---------|
| Fnd: | C 53.24 | H 5.97 | Br 25.21 |         | c) N-(2-Hydroxyethyl)-2,4-bis-(4-methoxybenzyl)-3-azaglutaric acid-di-tert-butyl ester 6.2 g (20 mmol) of the bromide of Example b) is dissolved at 0° C. in 15 ml of N,N-dimethylformamide and mixed with 2.2 g (22 mmol) of potassium bicarbonate. Then, 0.54 g (8.9 mmol) of ethanolamine is added, stirred for 30 minutes at low temperature and then for three days at room temperature. The batch is mixed with 100 ml of tert-butyl methyl ether, extracted with saturated sodium bicarbonate solution and saturated common salt solution, and the organic phase is dried on sodium sulfate. After the filtration, it is evaporated to dryness.

Yield: 5.8 g (49% of theory) of colorless oil, which slowly crystallizes completely.

Analysis (relative to solventless substance):

| Cld: | C 68.03 | H 8.18 | N 2.64 | O 21.14 |
|------|---------|--------|--------|---------|
| Fnd: | C 67.76 | H 8.23 | N 2.88 |         | d) N-(2-Bromoethyl)-2,4-bis-(4-methoxybenzyl)-3-azaglutaric acid-di-tert-butyl ester From 5.6 g (10.6 mmol) of the diester of Example c) and triphenylphosphine and N-bromosuccinimide, the bromide is obtained as pale yellow oil analogously to Example 1e).

Yield: 5.12 g (81.5% of theory)

Analysis (relative to solventless substance):

| Cld: | C 60.81 | H 7.14 | Br 13.48 | N 2.36 | O 16.20 |
|------|---------|--------|----------|--------|---------|
| Fnd: | C 60.70 | H 7.08 | Br 13.29 | N 2.44 |         | e) 3,6,9-Triaza-6-(tert-butoxycarbonylmethyl)-3,9-bis-[2-(4-methoxyphenyl)-1-(tert-butoxycarbonyl)-ethyl]-2,10-bis-(4-methoxybenzyl)-undecanedioic acid-di-tert-butyl ester 4.85 g (8.2 mmol) of the bromide produced according to Example d) and 0.67 g (4 mmol) of glycine-tert-butyl ester-hydrochloride are introduced into 35 ml of acetonitrile and mixed with 20 ml of 2N phosphate buffer solution (pH 8.0). The batch is vigorously stirred at room temperature for 30 hours, and the aqueous phosphate buffer phase is exchanged for fresh buffer solution after 2 and 18 hours. Then, the organic phase is concentrated by evaporation in a vacuum, and the residue is chromatographed on silica gel with hexane/diethyl ether/triethylamine. The product-containing fractions are concentrated by evaporation in a vacuum.

Yield: 4.1 g (88.8% of theory) of colorless oil.

Analysis (relative to solventless substance):

| Cld: | C 68.66 | H 8.29 | N 3.64 | O 19.40 |
|------|---------|--------|--------|---------|
| Fnd: | C 68.73 | H 8.31 | N 3.50 |         | f) Terbium complex of the disodium salt of 3,6,9-triaza-6-(carboxymethyl)-3,9-bis-[2-(4-methoxyphenyl)-1-carboxyethyl}-2,10-bis-(4-methoxybenzyl)-undecanedioic acid 3.9 g (3.4 mmol) of the pentaester produced according to Example e) is dissolved in 15 ml of tetrahydrofuran and mixed with 15 ml of 2N sodium hydroxide solution, it is stirred for three hours at 55° C., adjusted to pH 1 with concentrated hydrochloric acid, greatly concentrated by evaporation in a rotary evaporator and the residue is purified by ion exchange chromatography (cationic exchanger ($H^+$ form), eluent: ammonia-water solution). The eluate is concentrated by evaporation and greatly dried under high vacuum, by which the free complexing agent is obtained. The penta acid is taken up in 100 ml of water and mixed with 0.85 g (1.7 mmol) of terbium carbonate hydrate. The suspension is stirred for 15 hours at 70° C. and filtered. Then, it is adjusted to pH 7.1 with 1N sodium hydroxide solution. Then, after the addition of 0.4 g of activated carbon, the solution is stirred at 90° C. for one hour and filtered. After freeze-drying, the filtrate yields a colorless solid.

Yield: 3.4 g (93.1% of theory)

Analysis (relative to anhydrous substance):

| Cld: | C 51.45 | H 4.69 | N 3.91 | O 20.86 | Tb 14.80 | Na 4.28 |
|------|---------|--------|--------|---------|----------|---------|
| Fnd: | C 51.27 | H 4.73 | N 3.76 |         | Tb 14.68 | Na 3.94 |

Example 8

Holmium complex of the disodium salt of 3,6,9-triaza-6,9-bis-(carboxymethyl)-3-[(4-methoxybenzyl)-carboxymethyl]-10-(4-ethoxybenzyl)-2-(4-methoxybenzyl)-undecanedioic acid a) N-Benzyl-N-(2-hydroxyethyl)-glycine-tert-butyl ester 15.1 g (100 mmol) of N-benzylethanolamine is dissolved in 50 ml of tetrahydrofuran and mixed with 15 ml of water and 13.8 g (100 mmol) of potassium carbonate. After instillation of 20.5 g (105 mmol) of bromoacetic acid-tert-butyl ester, it is stirred for 6 hours at 65° C. After cooling, it is filtered, concentrated by evaporation in a vacuum and the residue is chromatographed on silica gel with diethyl ether/hexane/triethylamine. The product fractions are concentrated by evaporation in a vacuum and dried.

Yield: 24.8 g (93.3% of theory) of colorless oil.

Analysis (relative to solventless substance):

| Cld: | C 67.90 | H 8.74 | N 5.28 | O 18.09 |
|------|---------|--------|--------|---------|
| Fnd: | C 67.87 | H 8.88 | N 5.19 |         | b) N-Benzyl-N-(2-bromoethyl)-glycine-tert-butyl ester

A solution of 20 g (75.4 mmol) of the compound described under a) and 22.9 g (87.1 mmol) of triphenylphosphine in 400 ml of dichloromethane is mixed at 0° C. in portions with 15.5 g (87.1 mmol) of N-bromosuccinimide and then stirred for 20 hours at room temperature. The solution is concentrated by evaporation and the residue is absorptively precipitated with tert-butyl methyl ether. A precipitate develops, which is separated and washed with tert-butyl methyl ether. The combined filtrates are concentrated by evaporation and the residue is chromatographed on silica gel with hexane/diethyl ether. The concentration by evaporation of the product fractions yields a colorless oil.

Yield: 20.3 g (81.7% of theory) of colorless oil.

| Analysis (relative to solventless substance): | | | | |
|---|---|---|---|---|
| Cld: | C 54.89 | H 6.76 | Br 24.34 | N 4.27 | O 9.75 |
| Fnd: | C 54.77 | H 6.81 | Br 24.12 | N 4.34 | | c) 2,4-Bis-(4-hydroxybenzyl)-3-azaglutaric acid-diisopropyl ester 9.01 g (50.0 mmol) of 4-hydroxyphenylpyruvic acid and 9.06 g (50.0 mmol) of tyrosine are dissolved in 60 ml of methanol and stirred for six hours at 60° C. Then, it is allowed to cool to room temperature and 0.76 g (20 mmol) of sodium borohydride is added. It is allowed to stir overnight and then the reaction mixture is mixed carefully with diluted hydrochloric acid until no more gas generation can be observed. The reaction mixture is concentrated by evaporation and dried in an oil pump vacuum for several hours at 100° C. The residue is taken up in isopropanol. Hydrogen chloride gas is introduced until saturation is achieved, stirred for two hours at room temperature and then for eight hours at 85° C. Then, it is concentrated by evaporation, the residue is dispersed between ethyl acetate and sodium bicarbonate solution, the organic phase is dried on sodium sulfate, filtered and concentrated by evaporation. The residue is chromatographed on silica gel with use of hexane/ethyl acetate as mobile solvent. The fractions that contain the pure product are combined and concentrated by evaporation.

Yield: 16.0 g (74.5% of theory) of pale yellow oil.

| Analysis (relative to solventless substance): | | | | |
|---|---|---|---|---|
| Cld: | C 67.11 | H 7.28 | N 3.26 | O 22.35 |
| Fnd: | C 67.04 | H 7.33 | N 3.16 | | d) N-(3-Aza-3-benzyl-4-tert-butoxycarbonyl-butyl)-2,4-bis-(4-hydroxybenzyl)-3-azaglutaric acid-diisopropyl ester 10.8 g (33.0 mmol) of the compound produced according to Example b) and 12.9 g (30 mmol) of the compound described in Example c) are introduced into 45 ml of acetonitrile and mixed with 25 ml of 2N phosphate buffer solution (pH 8.0). The batch is vigorously stirred at room temperature for 22 hours, and the aqueous phosphate buffer phase is exchanged for fresh buffer solution after 2 and 7 hours. Then, the organic phase is concentrated by evaporation in a vacuum and the residue is chromatographed on silica gel with hexane/ethyl acetate/triethylamine. The product-containing fractions are concentrated by evaporation in a vacuum.

Yield: 13.9 g (68.3% of theory) of colorless oil.

| Analysis (relative to solventless substance): | | | | |
|---|---|---|---|---|
| Cld: | C 69.21 | H 7.74 | N 4.14 | O 18.91 |
| Fnd: | C 69.13 | H 7.78 | N 4.16 | | e) N-(3-Aza-3-benzyl-4-tert-butoxycarbonyl-butyl)-2,4-bis-(4-methoxybenzyl)-3-azaglutaric acid-diisopropyl ester 12.5 g (18.5 mmol) of the compound described in Example d) is dissolved in 50 ml of anhydrous N,N-dimethylformamide and mixed at 0° C. under argon with 1.60 g (40.0 mmol) of sodium hydride dispersion (60% in mineral oil). The batch is allowed to stir for 15 minutes, then 6.81 g (48.0 mmol) of methyl iodide is added, the reaction temperature is allowed to increase to room temperature and it is stirred for another four hours. For working-up, the batch is taken up in toluene and shaken out several times against aqueous sodium bicarbonate solution. The organic phase is separated, dried on magnesium sulfate, filtered and concentrated by evaporation. The oily residue is chromatographed on silica gel with hexane/diethyl ether/triethylamine, the product-containing fractions are combined and concentrated by evaporation.

Yield: 11.6 g (89.2% of theory) of colorless oil.

| Analysis (relative to solventless substance): | | | | |
|---|---|---|---|---|
| Cld: | C 69.86 | H 8.01 | N 3.97 | O 18.16 |
| Fnd: | C 69.78 | H 8.23 | N 3.78 | | f) N-(3-Aza-4-tert-butoxycarbonyl-butyl)-2,4-bis-(4-methoxybenzyl)-3-azaglutaric acid-diisopropyl ester 11.0 g (15.5 mmol) of the compound produced according to Example e) is dissolved in 50 ml of ethanol and after the addition of 1.0 g of palladium (10%) on activated carbon, it is hydrogenated under hydrogen atmosphere at room temperature until hydrogen absorption is completed. After filtration and concentration by evaporation of the filtrate in a vacuum, a colorless oil is obtained.

Yield: 9.35 g (97.5% of theory)

| Analysis (relative to solventless substance): | | | | |
|---|---|---|---|---|
| Cld: | C 66.43 | H 8.20 | N 4.56 | O 20.82 |
| Fnd: | C 66.54 | H 8.33 | N 4.46 | | g) N-[3-Aza-4-tert-butoxycarbonyl-3-(2-hydroxyethyl)-butyl]-2,4-bis-(4-methoxybenzyl)-3-azaglutaric acid-diisopropyl ester 8.99 g (14.6 mmol) of the compound described in Example f) is dissolved in 30 ml of tetrahydrofuran and mixed with 2 ml of water and 2.02 g (14.6 mmol) of potassium carbonate. After instillation of 2.2 g (17.5 mmol) of bromoethanol, it is stirred for 6 hours at 65° C. After cooling, it is filtered, concentrated by evaporation in a vacuum and the residue is chromatographed on silica gel with diethyl ether/hexane/triethylamine. The product fractions are concentrated by evaporation in a vacuum and dried.

Yield: 7.84 g (81.4% of theory) of colorless oil.

| Analysis (relative to solventless substance): | | | | |
|---|---|---|---|---|
| Cld: | C 65.63 | H 8.26 | N 4.25 | O 21.86 |
| Fnd: | C 65.78 | H 8.40 | N 4.11 | | h) N-[3-Aza-4-tert-butoxycarbonyl-3-(2-bromoethyl)-butyl]-2,4-bis-(4-methoxybenzyl)-3-azaglutaric acid-diisopropyl ester A solution of 7.73 g (11.7 mmol) of the compound described under Example g) and 3.39 g (12.9 mmol) of triphenylphosphine in 50 ml of dichloromethane is mixed at 0° C. in portions with 2.30 g (12.9 mmol) of N-bromosuccinimide and then stirred for 20 hours at room temperature. The solution is concentrated by evaporation and the residue is absorptively precipitated with hexane. A precipitate develops, which is separated and washed with hexane. The combined filtrates are concentrated by evaporation and the residue is chromatographed on silica gel with hexane/diethyl ether. The concentration by evaporation of the product fractions yields a colorless oil.

Yield: 7.07 g (83.5% of theory) of colorless oil.

| Analysis (relative to solventless substance): | | | | | |
|---|---|---|---|---|---|
| Cld: | C 59.91 | H 7.40 | Br 11.07 | N 3.88 | O 17.74 |
| Fnd: | C 60.04 | H 7.52 | Br 10.89 | N 3.95 | | i) N-Benzyl-tyrosine-tert-butyl ester 16.9 g (71.5 mmol) of tyrosine-tert-butyl ester and 8.33 g (78.6 mmol) of benzaldehyde are stirred in 50 ml of methanol for 3 hours at 24° C. and then mixed with 3.37 g (53.6 mmol) of sodium cyanoborohydride. After 24 hours of stirring at room temperature, the batch is adjusted to pH 2 by careful addition of semiconcentrated hydrochloric acid, then neutralized with concentrated aqueous sodium bicarbonate solution and after substantial evaporation of methanol with ethyl acetate, it is shaken out. The organic phase is dried on anhydrous magnesium sulfate, filtered and concentrated by evaporation. The residue is chromatographed on silica gel with diethyl ether/hexane/triethylamine; the product-containing fractions are combined and concentrated by evaporation.

Yield: 15.7 g (67% of theory) of colorless oil.

| Analysis (relative to solventless substance): | | | | |
|---|---|---|---|---|
| Cld: | C 73.37 | H 7.70 | N 4.28 | O 14.66 |
| Fnd: | C 73.25 | H 7.84 | N 4.16 | | j) N-Benzyl-2-(4-hydroxybenzyl)-3-azaglutaric acid-di-tert-butyl ester 15.1 g (46.1 mmol) of N-benzyl-tyrosine-tert-butyl ester (Example i) is dissolved in 50 ml of tetrahydrofuran and mixed with 5 ml of water and 9.54 g (69 mmol) of potassium carbonate. After instillation of 9.89 g (51 mmol) of bromoacetic acid-tert-butyl ester, it is stirred for two days at 65° C. After cooling, it is filtered, concentrated by evaporation in a vacuum and the residue is chromatographed on silica gel with diethyl ether/hexane/triethylamine. The product fractions are concentrated by evaporation in a vacuum and dried.

Yield: 14.9 g (73.3% of theory) of colorless oil.

| Analysis (relative to solventless substance): | | | | |
|---|---|---|---|---|
| Cld: | C 74.33 | H 8.22 | N 3.94 | O 13.50 |
| Fnd: | C 74.27 | H 8.26 | N 3.74 | | k) N-Benzyl-2-(4-ethoxybenzyl)-3-azaglutaric acid-di-tert-butyl ester 13.2 g (30 mmol) of N-benzyl-2-(4-hydroxybenzyl)-3-azaglutaric acid-di-tert-butyl ester (Example j) is dissolved in 50 ml of anhydrous N,N-dimethylformamide and mixed at 0° C. under argon with 1.31 g (33 mmol) of sodium hydride dispersion (60% in mineral oil). The batch is allowed to stir for 15 minutes, then 8.05 g (51.7 mmol) of ethyl iodide is added, the reaction temperature is allowed to increase to room temperature and it is stirred for another three hours. For working-up, the batch is taken up in toluene and shaken out several times against aqueous sodium bicarbonate solution. The organic phase is separated, dried on magnesium sulfate, filtered and concentrated by evaporation. The oily residue is chromatographed for purification on silica gel with hexane/diethyl ether/triethylamine. The product fractions are concentrated by evaporation in a vacuum and dried.

Yield: 12.7 g (90.3% of theory) of colorless oil.

| Analysis (relative to solventless substance): | | | | |
|---|---|---|---|---|
| Cld: | C 71.61 | H 8.37 | N 2.98 | O 17.03 |
| Fnd: | C 71.72 | H 8.43 | N 2.87 | | l) 2-(4-Ethoxybenzyl)-3-azaglutaric acid-di-tert-butyl ester 14.2 g (30.2 mmol) of the compound produced according to Example k) is dissolved in 75 ml of ethanol, and after the addition of 1.4 g of palladium (10%) on activated carbon, it is hydrogenated under hydrogen atmosphere at room temperature until hydrogen absorption is completed. After filtration and concentration by evaporation of the filtrate in a vacuum, a colorless oil is obtained.

Yield: 11.3 g (98.6% of theory)

| Analysis (relative to solventless substance): | | | | |
|---|---|---|---|---|
| Cld: | C 66.46 | H 8.77 | N 3.69 | O 21.08 |
| Fnd: | C 66.44 | H 8.63 | N 3.57 | | m) 3,6,9-Triaza-3,6-bis-(tert-butoxycarbonylmethyl)-2-(4-ethoxybenzyl)-9,9-bis-[2-(4-methoxyphenyl)-1-((1-methylethoxy)-carbonyl)-ethyl]-nonanoic acid-tert-butyl ester 6.85 g (9.49 mmol) of the compound produced according to Example h) and 3.60 g (9.49 mmol) of the compound described in Example 1) are introduced into 15 ml of acetonitrile and mixed with 7.5 ml of 2N phosphate buffer solution (pH 8.0). The batch is vigorously stirred at room temperature for 22 hours, and the aqueous phosphate buffer phase is exchanged for fresh buffer solution after 2 and 7 hours. Then, the organic phase is concentrated by evaporation in a vacuum, and the residue is chromatographed on silica gel with hexane/ethyl acetate/triethylamine. The product-containing fractions are concentrated by evaporation in a vacuum.

Yield: 6.26 g (64.6% of theory) of colorless oil.

| Analysis (relative to solventless substance): | | | |
|---|---|---|---|
| Cld: | C 67.10 | H 8.40 | N 4.12 | O 20.38 |
| Fnd: | C 67.21 | H 8.54 | N 4.17 | | n) Holmium complex of the disodium salt of 3,6,9-triaza-6,9-bis-(carboxymethyl)-3-[(4-methoxybenzyl)-carboxymethyl]-10-(4-ethoxybenzyl)-2-(4-methoxybenzyl)-undecanedioic acid 6.11 g (5.99 mmol) of the compound produced according to Example m) is dissolved in 20 ml of tetrahydrofuran and mixed with 24 ml of 2N sodium hydroxide solution, it is stirred for two hours at 60° C., adjusted to pH 1 with concentrated hydrochloric acid, greatly concentrated by evaporation in a rotary evaporator and the residue is purified by ion exchange chromatography (cationic exchanger ($H^+$ form), eluent: ammonia-water solution). The eluate is concentrated by evaporation and greatly dried under high vacuum, by which the free complexing agent is obtained. The penta acid is taken up in 250 ml of water and mixed with 1.13 g (2.99 mmol) of holmium oxide. The suspension is stirred for 16 hours at 100° C. and filtered. Then, it is adjusted to pH 7.3 with 1N sodium hydroxide solution. Then, after the addition of 0.6 g of activated carbon, the solution is stirred at 80° C. for one hour and filtered. After freeze-drying, the filtrate yields a colorless solid.

Yield: 5.55 g (95.3% of theory)

| Analysis (relative to anhydrous substance): | | | | | |
|---|---|---|---|---|---|
| Cld: | C 48.11 | H 4.56 | N 4.32 | O 21.36 | Ho 16.94 | Na 4.72 |
| Fnd: | C 48.12 | H 4.64 | N 4.21 | | Ho 16.76 | Na 4.55 |

Example 9

Erbium complex of the disodium salt of 3,6,9-triaza-3,6,9-tris-(carboxymethyl)-2,10-bis-(4-ethoxybenzyl)-4,8-bis-(4-propoxybenzyl)-undecanedioic acid a) α-Oxo-4-ethoxyphenylacetic acid-propyl ester 10.4 g (50 mmol) of α-oxo-4-ethoxyphenylacetic acid (Bandyopahyay et al., J. Ind. Chem. Soc. 66(4), 239, 1989) and 1.0 g of p-toluenesulfonic acid-monohydrate are refluxed into a mixture of 100 ml of toluene and 50 ml of N-propanol while in a water separator until no more water separates out. Then, it is concentrated by evaporation in a vacuum, the residue is dispersed between ethyl acetate and sodium bicarbonate solution, the organic phase is dried on magnesium sulfate, filtered and concentrated by evaporation.

Yield: 10.9 g (87.3% of theory) of yellowish oil.

| Analysis (relative to solventless substance): | | | |
|---|---|---|---|
| Cld: | C 67.18 | H 7.25 | O 25.57 |
| Fnd: | C 67.33 | H 7.32 | | b) 3-Aza-2-(4-ethoxybenzyl)-5-hydroxy-4-(4-propoxybenzyl)-valeric acid-propyl ester 10.1 g (40.4 mmol) of the compounds described in Example a) and 8.44 g (40.4 mmol) of the compounds described in Example 6c) are stirred in 80 ml of methanol for two hours at 50° C. Then, 0.76 g (20.2 mmol) of sodium borohydride is added in portions at 0° C. It is allowed to stir overnight and then the reaction mixture is carefully mixed with diluted hydrochloric acid until no more gas generation can be observed. The reaction mixture is concentrated by evaporation and the residue is dispersed between ethyl acetate and sodium bicarbonate solution, the organic phase is dried on sodium sulfate, filtered and concentrated by evaporation. The residue is chromatographed on silica gel with use of hexane/ethyl acetate as mobile solvent. The fractions that contain the pure product are combined and concentrated by evaporation.

Yield: 14.1 g (78.7% of theory) of pale yellow oil.

| Analysis (relative to solventless substance): | | | |
|---|---|---|---|
| Cld: | C 70.40 | H 8.41 | N 3.16 | O 18.03 |
| Fnd: | C 70.28 | H 8.53 | N 3.17 | | c) 3-Aza-2-(4-ethoxybenzyl)-5-hydroxy-4-(4-propoxybenzyl)-3-(tert-butoxycarbonylmethyl)-valeric acid-propyl ester 13.6 g (30.7 mmol) of the compound described under Example b) is dissolved in 150 ml of toluene. 4.24 g (30.7 mmol) of powdered potassium carbonate and 6.58 g (33.7 mmol) of bromoacetic acid-tert-butyl ester are added and stirred until the reaction is completed at an internal temperature of 70° C. Then, it is filtered, concentrated by evaporation, and the residue is chromatographed on silica gel with hexane/ethyl acetate. The fractions that contain the pure product are combined and concentrated by evaporation in a vacuum.

Yield: 12.4 g (72.6% of theory) of yellowish oil.

| Analysis: | | | |
|---|---|---|---|
| Cld: | C 68.91 | H 8.49 | N 2.51 | O 20.08 |
| Fnd: | C 70.06 | H 8.55 | N 2.24 | | d) 3-Aza-5-bromo-2-(4-ethoxybenzyl)-4-(4-propoxybenzyl)-3-(tert-butoxycarbonylmethyl)-valeric acid-propyl ester A solution of 12.0 g (21.5 mmol) of the compound described under Example c) and 6.21 g (23.7 mmol) of triphenylphosphine in 70 ml of dichloromethane is mixed at 0° C. in portions with 4.21 g (23.7 mmol) of N-bromosuccinimide and then stirred for 20 hours at room temperature. The solution is concentrated by evaporation and the residue is absorptively precipitated with hexane. A precipitate develops, which is separated and washed with hexane. The combined filtrates are concentrated by evaporation and the residue is chromatographed on silica gel with hexane/diethyl ether. The concentration by evaporation of the product fractions yields a colorless oil.

Yield: 10.9 g (81.4% of theory) of colorless oil.

| Analysis (relative to solventless substance): | | | | |
|---|---|---|---|---|
| Cld: | C 61.93 | H 7.47 | Br 12.88 | N 2.26 | O 15.47 |
| Fnd: | C 62.14 | H 7.31 | Br 12.69 | N 2.42 | | e) 3,6,9-Triaza-3,6,9-tris-(tert-butoxycarbonylmethyl)-2,10-bis-(4-ethoxybenzyl)-4,8-bis-(4-propoxybenzyl)-undecanedioic acid-dipropyl ester 10.5 g (16.9 mmol) of the compound produced according to Example d) and 1.11 g (8.46 mmol) of glycine-tert-butyl ester are introduced into 30 ml of acetonitrile and mixed with 15 ml of 2N phosphate buffer solution (pH 8.0). The batch is vigorously stirred at room temperature for 22 hours, and the aqueous phosphate buffer phase is exchanged for fresh buffer solution after 2 and 7 hours. Then, the organic phase is concentrated by evaporation in a vacuum and the residue is chromatographed on silica gel with hexane/ethyl acetate/triethylamine. The product-containing fractions are concentrated by evaporation in a vacuum.

Yield: 6.83 g (66.7% of theory) of colorless oil.

| Analysis (relative to solventless substance): | | | | |
|---|---|---|---|---|
| Cld: | C 69.45 | H 8.58 | N 3.47 | O 18.50 |
| Fnd: | C 69.27 | H 8.50 | N 3.59 | | f) Erbium complex of the disodium salt of 3,6,9-triaza-3,6,9-tris-(carboxymethyl)-2,10-bis-(4-ethoxybenzyl)-4,8-bis-(4-propoxybenzyl)-undecanedioic acid 6.64 g (5.48 mmol) of the compound produced according to Example e) is dissolved in 20 ml of tetrahydrofuran and mixed with 24 ml of 2N sodium hydroxide solution, it is stirred for two hours at 60° C., adjusted to pH 1 with concentrated hydrochloric acid, greatly concentrated by evaporation in a rotary evaporator and the residue is purified by ion exchange chromatography (cationic exchanger ($H^+$ form), eluent: ammonia-water solution). The eluate is concentrated by evaporation and greatly dried under high vacuum, by which the free complexing agent is obtained.

The penta acid is taken up in 250 ml of water and mixed with 1.04 g (2.74 mmol) of erbium oxide. The suspension is stirred for 16 hours at 100° C. and filtered. Then, it is adjusted to pH 7.3 with 1N sodium hydroxide solution. Then, after the addition of 0.6 g of activated carbon, the solution is stirred at 80° C. for one hour and filtered. After freeze-drying, the filtrate yields a colorless solid.

Yield: 5.78 g (90.3% of theory)

| Analysis (relative to anhydrous substance): | | | | | | |
|---|---|---|---|---|---|---|
| Cld: | C 53.55 | H 5.36 | N 3.60 | O 19.20 | Er 14.34 | Na 3.94 |
| Fnd: | C 53.63 | H 5.42 | N 3.51 | | Er 14.21 | Na 3.77 |

Example 10

Study of acute toxicity ($LD_{50}$) after one-time intravenous administration to mice The contrast medium to be tested was administered to the mice in individual restraining cages (strain: NMRI (SPF); cultivator: Schering; average weight: 20 g; same sex distribution) into one of the caudal veins at a rate of 2 ml/minutes and at different dosage levels. The number of animals that died up to a fixed time was determined (3 hours, 24 hours, 3 days and 7 days).

The $LD_{50}$ for the ytterbium complex according to Example 4e is approximately 15 mmol/kg of body weight.

Example 11

Lutetium complex of the disodium salt of 3,6,9-triaza-3,6,9-tris-(carboxymethyl)-5-(4-ethoxybenzyl)-undecanedioic acid a) 3,6,9-Triaza-3,6,9-tris-(tert-butoxycarbonylmethyl)-5-(4-ethoxybenzyl)-undecanedioic acid-di-tert-butyl ester 16.7 g (21.4 mmol) of 3,6,9-triaza-3,6,9-tris-(tert-butoxycarbonylmethyl)-5-(4-hydroxybenzyl)-undecanedioic acid-di-tert-butyl ester (DOS 3710730) is dissolved in 50 ml of anhydrous N,N-dimethylformamide and mixed at 0° C. under argon with 0.94 g (23.5 mmol) of sodium hydride dispersion (60% in mineral oil). The batch is allowed to stir for 15 minutes, then 3.74 g (24.0 mmol) of ethyl iodide is added, the reaction temperature is allowed to increase to room temperature, and it is stirred for another four hours. For working-up, the batch is taken up in toluene and shaken out several times against aqueous sodium bicarbonate solution. The organic phase is separated, dried on magnesium sulfate, filtered and concentrated by evaporation. The oily residue is chromatographed on silica gel with hexane/diethyl ether/triethylamine, the product-containing fractions are combined and concentrated by evaporation.

Yield: 16.4 g (94.8% of theory) of colorless oil.

| Analysis (relative to solventless substance): | | | | |
|---|---|---|---|---|
| Cld: | C 63.92 | H 9.11 | N 5.20 | O 21.78 |
| Fnd: | C 63.77 | H 9.28 | N 5.13 | | b) Lutetium complex of the disodium salt of 3,6,9-triaza-3,6,9-tris-(carboxymethyl)-5-(4-ethoxybenzyl)-undecanedioic acid 16.1 g (20 mmol) of the compound produced according to Example a) is dissolved in 50 ml of tetrahydrofuran and mixed with 60 ml of 2N sodium hydroxide solution, it is stirred for two hours at 60° C., adjusted to pH 1 with concentrated hydrochloric acid, greatly concentrated by evaporation in a rotary evaporator and the residue is purified by ion exchange chromatography (cationic exchanger ($H^+$ form), eluent: ammonia-water solution). The eluate is concentrated by evaporation and greatly dried under high vacuum, by which the free complexing agent is obtained.

The penta acid is taken up in 250 ml of water and mixed with 3.98 g (10 mmol) of lutetium oxide. The suspension is stirred for 36 hours at 100° C. and filtered. Then, it is adjusted to pH 7.3 with 1N sodium hydroxide solution. Then, after the addition of 1.6 g of activated carbon, the solution is stirred for one hour at 80° C. and filtered. After freeze-drying, the filtrate yields a colorless solid.

Yield: 14.1 g (94.8% of theory)

| Analysis (relative to anhydrous substance): | | | | | | |
|---|---|---|---|---|---|---|
| Cld: | C 37.16 | H 3.80 | N 5.65 | O 23.67 | Lu 23.53 | Na 6.18 |
| Fnd: | C 37.03 | H 3.94 | N 5.51 | | Lu 23.38 | Na 5.90 |

Example 12

Ytterbium complex of the disodium salt of 3,6,9-triaza-3,6,9-tris-(carboxymethyl)-4-(2-ethoxybenzyl)-undecanedioic acid a) N-Benzyloxycarbonyl-3-[2-hydroxyphenyl]-alanine-methyl ester 9.5 g (52.4 mmol) of o-tyrosine (2-hydroxyphenylalanine, Heraeus) is suspended in 48 ml of methanol, cooled in an ice bath and mixed drop by drop with 7.6 ml (105 mmol) of thionyl chloride. After one hour, the batch is heated to reflux temperature and stirred for three hours. Then, it is allowed to stir overnight at room temperature. It is evaporated to dryness, the residue is taken up in methanol, concentrated by evaporation and the process is repeated twice. It is taken up in 50 ml of water, adjusted to pH 8.5 with 1.5 molar sodium carbonate solution and 22.1 ml (63 mmol) of benzyl chloroformate is added under pH control. It is stirred for four hours at room temperature, the organic phase is separated, it is washed with water and dried on sodium sulfate. After the concentration by evaporation, the residue is chromatographed on silica gel (methylene chloride/ethyl acetate).

Yield: 13.5 g (78.2 of theory) of colorless oil, which slowly crystallizes.

| Analysis (relative to solventless substance): | | | | |
|---|---|---|---|---|
| Cld: | C 65.64 | H 5.82 | N 4.25 | O 24.29 |
| Fnd: | C 65.57 | H 5.68 | N 4.30 | | b) N-Benzyloxycarbonyl-3-[2-ethoxyphenyl]-alanine-methyl ester 10.2 g (31 mmol) of the ortho-phenol of Example a) is dissolved at 40° C. in 6 ml of N,N-dimethylformamide, mixed with 9.2 g (66.5 mmol) of potassium carbonate and 0.3 ml of water. Then, 5.7 ml (43.4 mmol) of diethyl sulfate is added to it drop by drop and stirred for 3.5 hours. 6.6 ml of ammonia is added, and the batch is allowed to stir for one hour. Then, it is mixed with some water and extracted with tert-butyl methyl ether. The organic phase is separated, washed with diluted sulfuric acid and water. It is dried on sodium sulfate, concentrated by evaporation after filtration and the residue is chromatographed on silica gel.

Yield: 8.2 g (74% of theory) of colorless oil.

| Analysis (relative to solventless substance): | | | | |
|---|---|---|---|---|
| Cld: | C 67.21 | H 6.49 | N 3.92 | O 22.38 |
| Fnd: | C 67.09 | H 6.53 | N 3.77 | | c) N-Benzyloxycarbonyl-2-[2-ethoxybenzyl]-2-aminoethanol 7.9 g (22 mmol) of N-benzyloxycarbonyl-3-[2-ethoxyphenyl]-alanine-methyl ester (Example b) is dissolved in 63 ml of tert-butyl methyl ether and mixed with 1.1 g (30.1 mmol) of sodium borohydride. At 5° C., 15 ml of methanol is added, and it is stirred for five hours at constant temperature. Then, 1.5 ml of acetic acid, dissolved in 5 ml of tetrahydrofuran, is added, mixed with 9 ml of water and stirred for ten minutes at room temperature. The organic phase is separated, washed with water and dried on sodium sulfate. The drying agent is suctioned off, the filtrate is concentrated by evaporation and the residue is chromatographed for purification on silica gel.

Yield: 7.25 g (100% of theory) of colorless oil, which quickly crystallizes completely.

| Analysis (relative to solventless substance): | | | | |
|---|---|---|---|---|
| Cld: | C 69.28 | H 7.04 | N 4.25 | O 19.43 |
| Fnd: | C 69.32 | H 7.00 | N 4.18 | | d) N-Benzyloxycarbonyl-2-[2-ethoxybenzyl]-1,4,7-triazaheptane, dihydrochloride 7.2 g (22 mmol) of the alcohol of Example c) is dissolved in 18 ml of tetrahydrofuran and mixed at room temperature with 4.9 ml (35 mmol) of triethylamine. 2.54 ml (32.6 mmol) of methanesulfonic acid chloride, dissolved in 2 ml of tetrahydrofuran, is added and stirred at 20° C. for six hours. Then, 22.2 ml (330 mmol) of ethylenediamine is instilled in it at a temperature between 30° C. and 45° C. It is heated to 50° C. and the batch is allowed to stir for four hours. Then, the reaction mixture is concentrated by evaporation, the residue is taken up in ethyl acetate and washed with water. The organic phase is cooled in an ice bath and mixed with concentrated hydrochloric acid. The resulting precipitate is suctioned off, washed with cold isopropanol and dried at 50° C.

Yield: 7.5 g (76.7% of theory) of colorless solid.

| Analysis (relative to solventless substance): | | | | | |
|---|---|---|---|---|---|
| Cld: | C 56.76 | H 7.03 | Cl 15.95 | N 9.45 | O 10.80 |
| Fnd: | C 56.62 | H 7.11 | Cl 15.80 | N 9.36 | | e) 2-[2-Ethoxybenzyl]-1,4,7-triazaheptane, dihydrochloride 7.2 g (16.2 mmol) of the Z-protected amine of Example d) is suspended in 72 ml of methanol, mixed with 1.08 g of palladium (10%) on activated carbon and 0.5 ml of water and hydrogenated at normal pressure, at room temperature. After hydrogen absorption is completed, the catalyst is filtered out and the filtrate is concentrated by evaporation.

Yield: 4.9 g (97.5% of theory) of colorless solid.

| Analysis (relative to solventless substance): | | | | | |
|---|---|---|---|---|---|
| Cld: | C 50.33 | H 8.12 | Cl 22.85 | N 13.54 | O 5.16 |
| Fnd: | C 50.17 | H 8.34 | Cl 23.11 | N 13.40 | | f) 3,6,9-Triaza-3,6,9-tris-(tert-butoxycarbonylmethyl)-4-(2-ethoxybenzyl)-undecanedioic acid-di-tert-butyl ester 11.2 g (81.5 mmol) of potassium carbonate is dissolved in 11 ml of water and mixed at 35° C. with 4.8 g (15.5 mmol) of triamine (Example e). 12.5 ml (85.3 mmol) of bromoacetic acid-tert-butyl ester is added drop by drop, and the batch is stirred for seven hours at 65° C. After 18 hours of stirring at room temperature, the reaction mixture is mixed with water and shaken out with ethyl acetate. The organic phase is dried on sodium sulfate, concentrated by evaporation and the residue is chromatographed on silica gel (methylene chloride/methanol). After the concentration by evaporation of the product-containing fractions, the pentaester is obtained as pale yellow oil.

Yield: 11.9 g (95% of theory)

| Analysis (relative to solventless substance): | | | | |
|---|---|---|---|---|
| Cld: | C 63.92 | H 9.11 | N 5.20 | O 21.78 |
| Fnd: | C 64.05 | H 9.23 | N 5.07 | | g) 3,6,9-Triaza-3,6,9-tris-(carboxymethyl)-4-(2-ethoxybenzyl)-undecanedioic acid 11.75 g (14.5 mmol) of the pentaester of Example f) is dissolved in 86 ml of methanol and reacted with 4.65 g (116.3 mmol) of sodium hydroxide in 7.1 ml of water. It is stirred for four hours at 65° C., then the methanol is evaporated, water is added and concentrated by evaporation again. It is taken up in water and adjusted to pH 1.8 with acid ion exchanger. After the exchanger is filtered out, the aqueous solution is largely concentrated by evaporation and the penta acid is purified via preparative HPLC (water/methanol/pH 2.5). The product-containing fractions are concentrated by evaporation, taken up again in water and freeze-dried.

Yield: 4.9 g (64% of theory)

Analysis (relative to solventless substance):

| | | | | |
|---|---|---|---|---|
| Cld: | C 52.37 | H 6.31 | N 7.97 | O 33.36 |
| Fnd: | C 52.19 | H 6.46 | N 7.88 | | h) Ytterbium complex of the disodium salt of 3,6,9-triaza-3,6,9-tris-(carboxymethyl)-4-(2-ethoxybenzyl)-undecanedioic acid 3.72 g (7.05 mmol) of the penta acid of Example g) is dissolved at 60° C. in 19 ml of water and mixed in portions with 1.85 g (3.53 mmol) of ytterbium carbonate. After complexing is completed, it is filtered, adjusted to pH 7.0, stirred with 0.2 g of activated carbon for ten minutes at 100° C., filtered again, and the filtrate is freeze-dried.

Yield: 4.6 g (88% of theory) of colorless lyophilizate.

Analysis (relative to anhydrous substance):

| | | | | | | |
|---|---|---|---|---|---|---|
| Cld: | C 37.26 | H 3.81 | N 5.67 | O 23.74 | Yb 23.34 | Na 6.20 |
| Fnd: | C 37.13 | H 4.02 | N 5.55 | | Yb 23.18 | Na 5.87 |

Example 13 a) Ytterbium complex of the dimeglumine salt of 3,6,9-triaza-3,6,9-tris-(carboxymethyl)-4-(4-ethoxybenzyl)-undecanedioic acid 2.9 g (5.5 mmol) of 3,6,9-triaza-3,6,9-tris-(carboxymethyl)-4-(4-ethoxybenzyl)-undecanedioic acid (EP 0405704, Example 8b) is suspended in 20 ml of water and complexed with 1.45 g (2.75 mmol) of ytterbium carbonate at 60° C. After reaction is completed, the batch is neutralized with methylglucamine. It is filtered and the metal complex is obtained by freeze-drying the filtrate.

Yield: 5.7 g (95.3% of theory) of colorless lyophilizate.

Analysis (relative to anhydrous substance):

| | | | | | |
|---|---|---|---|---|---|
| Cld: | C 40.85 | H 5.93 | N 6.44 | O 30.88 | Yb 15.90 |
| Fnd: | C 40.67 | H 6.08 | N 6.17 | | Yb 15.62 | b) Ytterbium complex of the di-(2-amino-1,3,4-butanetriol) salt of 3,6,9-triaza-3,6,9-tris-(carboxymethyl)-4-(4-ethoxybenzyl)-undecanedioic acid The title compound is obtained analogously to Example a), if the complex acid is neutralized with 2-amino-1,3,4-butanetriol.

c) Cerium complex of the disodium salt of 3,6,9-triaza-3,6,9-tris-(carboxymethyl)-4-(4-ethoxybenzyl)-undecanedioic acid The title compound is obtained analogously to Example a), if the ligands (EP 0405704, Example 8b) are reacted with cerium carbonate and neutralized with sodium hydroxide solution.

d) Ytterbium complex of the disodium salt of 3,6,9-triaza-3,6,9-tris-(carboxymethyl)-4-(4-ethoxybenzyl)-undecanedioic acid 2.1 g (4 mmol) of 3,6,9-triaza-3,6,9-tris-(carboxymethyl)-4-(4-ethoxybenzyl)-undecanedioic acid (EP 0405704, Example 8b) is suspended in 15 ml of water and complexed with 1.05 g (2 mmol) of ytterbium carbonate at 60° C. After complexing is completed, the batch is neutralized with 1N sodium hydroxide solution. The complex solution is filtered and the title compound is obtained by freeze-drying the filtrate.

Yield: 3.0 g (100% of theory) of colorless lyophilizate.

Analysis (relative to anhydrous substance):

| | | | | | | |
|---|---|---|---|---|---|---|
| Cld: | C 37.26 | H 3.81 | N 5.67 | O 23.74 | Yb 23.34 | Na 6.20 |
| Fnd: | C 37.14 | H 4.11 | N 5.50 | | Yb 23.22 | Na 5.94 | e) Lutetium complex of the disodium salt of 3,6,9-triaza-3,6,9-tris-(carboxymethyl)-4-(4-ethoxybenzyl)-undecanedioic acid 3.0 g (5.7 mmol) of 3,6,9-triaza-3,6,9-tris-(carboxymethyl)-4-(4-ethoxybenzyl)-undecanedioic acid (EP 0405704, Example 8b) is suspended in 15 ml of water and complexed with 1.07 g (2.7 mmol) of lutetium oxide at 95° C. After complexing is completed, the batch is neutralized with 1N sodium hydroxide solution. The solution is filtered and the title compound is obtained by freeze-drying the filtrate.

Yield: 3.9 g (92% of theory) of colorless lyophilizate.

Analysis (relative to anhydrous substance):

| | | | | | | |
|---|---|---|---|---|---|---|
| Cld: | C 37.16 | H 3.80 | N 5.65 | O 23.67 | Lu 23.53 | Na 6.18 |
| Fnd: | C 37.02 | H 4.01 | N 5.53 | | Lu 23.36 | Na 5.87 |

In an analogous way, the corresponding bismuth complex (consisting of bismuth oxycarbonate), the hafnium complex (consisting of hafnium hydroxide), the lead complex (consisting of lead carbonate), the lanthanum complex (consisting of lanthanum carbonate), the dysprosium complex (consisting of dysprosium oxide), the erbium complex (consisting of erbium carbonate), the terbium complex (consisting of terbium carbonate), the holmium complex (consisting of holmium carbonate) and the praseodymium complex (consisting of praseodymium carbonate) are obtained.

Example 14

Gadolinium complex of the disodium salt of 3,6,9-triaza-3,6,9-tris-(carboxymethyl)-4-(2-butoxybenzyl)-undecanedioic acid a) N-Benzyloxycarbonyl-3-[2-butoxyphenyl]-alanine-methyl ester 5.0 g (15.2 mmol) of the ortho-phenol of Example 12a) is dissolved at 40° C. in 4 ml of N,N-dimethylformamide, mixed with 4.5 g (31.1 mmol) of potassium carbonate and 0.2 ml of water. Then, 2.1 g (15.5 mmol) of N-butyl bromide is added to it drop by drop, and it is stirred for 5 hours. 3.2 ml of ammonia is added and the batch is allowed to stand for one hour. Then, it is mixed with some water and extracted with tert-butyl methyl ether. The organic phase is separated, washed with diluted sulfuric acid and water. It is dried on sodium sulfate, concentrated by evaporation after the filtration and the residue is chromatographed on silica gel.

Yield: 4.7 g (80.2% of theory) of colorless oil.

Analysis (relative to solventless substance):

| | | | | |
|---|---|---|---|---|
| Cld: | C 68.55 | H 7.06 | N 3.63 | O 20.75 |
| Fnd: | C 68.42 | H 7.18 | N 3.59 | | b) N-Benzyloxycarbonyl-2-[2-butoxybenzyl]-2-aminoethanol 3.9 g (11 mmol) of N-benzyloxycarbonyl-3-[2-butoxyphenyl]-alanine-methyl ester (Example a) is dissolved in 30 ml of tert-butyl methyl ether and mixed with 0.55 g (15 mmol) of sodium borohydride. At 3° C., 8 ml of methanol is added, and it is stirred for five hours at constant temperature. Then, 0.8 ml of acetic acid, dissolved in 3 ml of tetrahydrofuran, is added, mixed with 5 ml of water and stirred for ten minutes at room temperature. The organic phase is separated, washed with water and dried on sodium sulfate. The drying agent is suctioned off, the filtrate is concentrated by evaporation and the residue is chromatographed for purification on silica gel.

Yield: 3.4 g (86.5% of theory) of colorless oil.

| Analysis (relative to solventless substance): | | | | |
|---|---|---|---|---|
| Cld: | C 70.56 | H 7.61 | N 3.92 | O 17.90 |
| Fnd: | C 70.43 | H 7.60 | N 4.07 | | c) N-Benzyloxycarbonyl-2-[2-butoxybenzyl]-1,4,7-triazaheptane, dihydrochloride 3.1 g (8.8 mmol) of the alcohol of Example b) is dissolved in 8 ml of tetrahydrofuran and mixed at room temperature with 2.0 ml (14 mmol) of triethylamine. 1.02 ml (13 mmol) of methanesulfonic acid chloride, dissolved in 1 ml of tetrahydrofuran, is added, and it is stirred at 20° C. for five hours. Then, 8.9 ml (132 mmol) of ethylenediamine is instilled in it at a temperature between 35° C. and 45° C. It is heated to 50° C. and the batch is allowed to stir for three hours. Then, the reaction mixture is concentrated by evaporation, the residue is taken up in ethyl acetate and washed with water. The organic phase is cooled in an ice bath and mixed with concentrated hydrochloric acid. The resulting precipitate is suctioned off, washed with cold isopropanol and dried at 50° C.

Yield: 3.8 g (91.4% of theory) of yellowish solid.

| Analysis (relative to solventless substance): | | | | | |
|---|---|---|---|---|---|
| Cld: | C 58.47 | H 7.47 | Cl 15.01 | N 8.89 | O 10.16 |
| Fnd: | C 58.28 | H 7.24 | Cl 14.93 | N 8.73 | | d) 2-[2-Butoxybenzyl]-1,4,7-triazaheptane, dihydrochloride 3.6 g (8.1 mmol) of the Z-protected amine of Example c) is suspended in 35 ml of methanol, mixed with 0.4 g of palladium (10%) on activated carbon and mixed with 0.3 ml of water and hydrogenated at normal pressure, at room temperature. After hydrogen absorption is completed, the catalyst is filtered out and the filtrate is concentrated by evaporation.

Yield: 2.4 g (87.6% of theory) of yellowish solid.

| Analysis (relative to solventless substance): | | | | | |
|---|---|---|---|---|---|
| Cld: | C 53.25 | H 8.64 | Cl 20.96 | N 12.42 | O 4.73 |
| Fnd: | C 53.08 | H 8.72 | Cl 21.23 | N 12.29 | | e) 3,6,9-Triaza-3,6,9-tris-(tert-butoxycarbonylmethyl)-4-(2-butoxybenzyl)-undecanedioic acid-di-tert-butyl ester 5.3 g (38.8 mmol) of potassium carbonate is dissolved in 5 ml of water and mixed at 35° C. with 2.3 g (7.4 mmol) of triamine-dihydrochloride (Example d). 5.9 ml (40.6 mmol) of bromoacetic acid-tert-butyl ester is added drop by drop, and the batch is stirred for eight hours at 60° C. After 15 hours of stirring at room temperature, the reaction mixture is mixed with water and shaken out with ethyl acetate. The organic phase is dried on sodium sulfate, concentrated by evaporation, and the residue is chromatographed on silica gel (ethyl acetate/acetone). After the concentration by evaporation of the product-containing fractions, the pentaester is obtained as colorless oil.

Yield: 5.3 g (85.7% of theory)

| Analysis (relative to solventless substance): | | | | |
|---|---|---|---|---|
| Cld: | C 64.64 | H 9.28 | N 5.03 | O 21.05 |
| Fnd: | C 64.77 | H 9.34 | N 4.88 | | f) 3,6,9-Triaza-3,6,9-tris-(carboxymethyl)-4-(2-butoxybenzyl)-undecanedioic acid 5.11 g (6.3 mmol) of the pentaester of Example e) is dissolved in 40 ml of methanol and reacted with 2.02 g (50.6 mmol) of sodium hydroxide in 3.1 ml of water. It is stirred for three hours at 55° C., then the methanol is evaporated, water is added and concentrated by evaporation again. It is taken up in water and adjusted to pH 1.9 with acid ion exchanger. After the exchanger is filtered out, the aqueous solution is largely concentrated by evaporation and the penta acid is purified via preparative HPLC (water/methanol/pH 2.8). The product-containing fractions are concentrated by evaporation, taken up again in water and freeze-dried.

Yield: 2.9 g (82.8% of theory) of colorless lyophilizate.

| Analysis (relative to solventless substance): | | | | |
|---|---|---|---|---|
| Cld: | C 4.05 | H 6.71 | N 7.56 | O 31.68 |
| Fnd: | C 53.91 | H 6.76 | N 7.39 | | g) Gadolinium complex of the disodium salt of 3,6,9-triaza-3,6,9-tris-(carboxymethyl)-4-(2-butoxybenzyl)-undecanedioic acid 2.48 g (4.7 mmol) of the penta acid of Example f) is suspended in 20 ml of water and mixed in portions with 0.85 g (2.35 mmol) of gadolinium oxide. After complexing is completed, it is filtered, adjusted to pH 7.2, stirred with 0.2 g of activated carbon for ten minutes at 90° C., filtered again and the filtrate is freeze-dried.

Yield: 3.5 g (98.8% of theory) of colorless lyophilizate.

| Analysis (relative to anhydrous substance): | | | | | | |
|---|---|---|---|---|---|---|
| Cld: | C 39.84 | H 4.28 | N 5.58 | O 23.35 | Gd 20.86 | Na 6.10 |
| Fnd: | C 39.73 | H 4.39 | N 5.47 | | Gd 20.71 | Na 5.94 |

Example 15

Ytterbium complex of the disodium salt of 3,6,9-triaza-3,6,9-tris-(carboxymethyl)-5-{4-[2-(2-ethoxyethoxy)-ethoxy]-benzyl}-undecanedioic acid a) 3,6,9-Triaza-3,6,9-tris-(tert-butoxycarbonylmethyl)-5-{4-[2-(2-ethoxyethoxy)-ethoxy]-benzyl}-undecanedioic acid-di-tert-butyl ester 16.7 g (21.4 mmol) of 3,6,9-triaza-3,6,9-tris-(tert-butoxycarbonylmethyl)-5-(4-hydroxybenzyl)-undecanedioic acid-di-tert-butyl ester (DOS 3710730) is dissolved in 50 ml of anhydrous N,N-dimethylformamide and mixed at 0° C. under argon with 0.94 g (23.5 mmol) of sodium hydride dispersion (60% in mineral oil). The batch is allowed to stir for 15 minutes, then 4.73 g (24.0 mmol) of 2-(2-ethoxyethoxy)-ethyl bromide is added, the reaction temperature is allowed to increase to room temperature and stirred for another four hours. For working-up, the batch is taken up in toluene and shaken out several times against aqueous sodium bicarbonate solution. The organic phase is separated, dried on magnesium sulfate, filtered and concentrated by evaporation. The oily residue is chromatographed on silica gel with hexane/diethyl ether/triethylamine, the product-containing fractions are combined and concentrated by evaporation.

Yield: 17.7 g (92.4% of theory) of colorless oil.

| Analysis (relative to solventless substance): | | | | |
|---|---|---|---|---|
| Cld: | C 62.99 | H 9.11 | N 4.69 | O 23.21 |
| Fnd: | C 63.07 | H 9.27 | N 4.75 | | b) Ytterbium complex of the disodium salt of 3,6,9-triaza-3,6,9-tris-(carboxymethyl)-5-{4-[2-(2-ethoxyethoxy)-ethoxy]-benzyl}-undecanedioic acid 13.4 g (15.0 mmol) of the compound produced according to Example a) is dissolved in 35 ml of tetrahydrofuran and mixed with 45 ml of 2N sodium hydroxide solution, it is stirred for two hours at 60° C., adjusted to pH 1 with concentrated hydrochloric acid, greatly concentrated by evaporation in a rotary evaporator and the residue is purified by ion exchange chromatography (cationic exchanger ($H^+$ form), eluent: ammonia-water solution). The eluate is concentrated by evaporation and greatly dried under high vacuum, by which the free complexing agent is obtained.

The penta acid is taken up in 150 ml of water and mixed with 3.94 g (7.5 mmol) of ytterbium carbonate. The suspension is stirred for 3 hours at 60° C. and filtered. Then, it is adjusted to pH 7.3 with 1N sodium hydroxide solution. Then, after the addition of 1.0 g of activated carbon, the solution is stirred for one hour at 80° C. and filtered. After freeze-drying, the filtrate yields a colorless solid.

Yield: 11.4 g (91.6% of theory)

| Analysis (relative to anhydrous substance): | | | | | | |
|---|---|---|---|---|---|---|
| Cld: | C 39.09 | H 4.37 | N 5.07 | O 25.07 | Yb 20.86 | Na 5.54 |
| Fnd: | C 38.84 | H 4.45 | N 5.02 | | Yb 20.69 | Na 5.30 |

Example 16

Density enhancement of the healthy liver parenchyma 10 and 60 minutes after infusion of a 0.25 molar solution of the gadolinium(III) complex of the 3,6,9-triaza-3,6,9-tris (carboxymethyl)-4-(4-ethoxybenzyl)-undecanedioic acid disodium salt (Gd-EOB-DTPA, described in Example 8c of EP 0405704) in the case of 5 human patients with liver metastases in a dose of 0.35 mmol/kg in Houndsfield units (HU). This dose corresponds to about 16 g of the complex per 70 kg of patient.

TABLE 3

| | 10 minutes p. inf. HU | 60 minutes p. inf. HU |
|---|---|---|
| Patient 1 | 19 | 26 |
| Patient 2 | 12 | 25 |
| Patient 3 | 10 | 17 |
| Patient 4 | 18 | 32 |
| Patient 5 | 15 | 32 |

In comparison, according to Mützel et al., 1982, the hexaiodinated SH L 433 (formula XI) that was specially developed for liver diagnosis

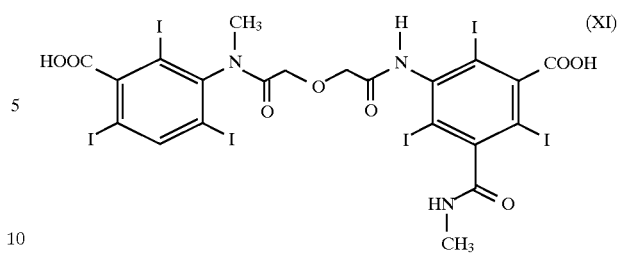

at a dose corresponding to 360 mg of iodine/kg (about 25 g of iodine per 70 kg of patient weight) produced an enhancement of only <10 HU (monkey, dog, mouse: >40 HU). The iotroxinate excreted via the bile ducts in about 90% of humans (hexaiodinated, 2 carboxyl groups) reaches only 15 HU in the liver in the case of the maximum compatible dose corresponding to about 7 g of iodine/70 kg of patient weight (Hübner, K. H.: Computertomographische Densitometrie von Leber, Milz und Nieren bei intravenös verabreichten lebergängigen Kontrastmitteln in Bolusform. [Computer Tomographic Densitometry of the Liver, Spleen and Kidneys in the Case of Intravenously-Administered Contrast Media That Pass Through the Liver in Bolus Form], Fortschr. Röntgenstr. [Research of X-Ray Radiation] 129, 289–297 (1978)).

In comparison, much greater X-ray absorption in the human liver is achieved with about 3.5 g of gadolinium in the form of a complex, which contains only one gadolinium ion/molecule, than with 25 g of iodine of SH L 433 (formula XI) or 7 g of iodine of the iotroxinate, although both these X-ray contrast media are hexaiodinated compounds.

Example 17

The following solution is produced:

0.1 mol of the holmium(III) complex of 3,6,9-triaza-3,6,9-tris-(carboxymethyl)-4-(4-butylbenzyl)-undecanedioic acid, dimeglumine salt, 0.005 mol of the calcium(II) complex of 3,6,9-triaza-3,6,9-tris-(carboxymethyl)-4-(4-butylbenzyl)-undecanedioic acid, trimeglumine salt in 1 liter of 5% mannitol solution, pH 7.0.

The solution is infused in a human patient for 30 minutes in a dosage of 0.3 mmol/kg of body weight. CT scans are performed before the beginning of the infusion, at the end of the infusion and 30 minutes after the end of the infusion in the usual way.

Example 18

3,6,9-Triaza-3,6,9-tris-(carboxymethyl)-4-(4-ethoxybenzyl)-undecanedioic acid

Disodium salt was complexed with different X-ray-absorbing metal ions and then in the case of differing concentration, the density values of the samples were measured in a water phantom since it approximately corresponded in dimensions to those of a human abdomen. The operation was performed in a commercially available computer tomograph with the commonly used voltage of 137 kV and 100 mA.

TABLE 4

Findings in Houndsfield units (HU ± SD)

| Element | Concentration (mmol/L) | HU | ± SD |
|---|---|---|---|
| H₂O | — | 14 | 23 |
| Gd | 50 | 218 | 23 |
|  | 500 | 1680 | 33 |
| Tb | 50 | 228 | 25 |
|  | 500 | 1760 | 45 |
| Dy | 50 | 226 | 23 |
|  | 500 | 1840 | 42 |
| Ho | 50 | 221 | 29 |
|  | 500 | 1890 | 40 |
| Er | 50 | 254 | 24 |
|  | 500 | 1955 | 57 |
| Yb | 50 | 252 | 18 |
|  | 500 | 1980 | 42 |
| I | 50 | 110 | 25 |
|  | 500 | 914 | 27 |

It turns out that there is a surprisingly high effectiveness of the rare earths relative to the iodine, which is attributable presumably to the special measuring conditions that exist in abdominal CT. Among the lanthanides, erbium, ytterbium and holmium are to be preferred over gadolinium and dysprosium, the elements that have been studied most to date.

Example 19

Execution of the Test

Fifteen human patients with known liver metastases were examined in the liver-CT 10 minutes, 60 minutes and (N=5) 120 minutes after intravenous infusion of 0.2, 0.35 or 0.5 mmol/kg of Gd-EOB-DTPA (see Example 16).

Gd-EOB-DTPA (0.25 mmol/L) was administered intravenously in an intravenous drip in the arm vein. The infusion time was 20 minutes for the dosages of 0.2 and 0.35 mmol/kg and 30 minutes for the maximum dose of 0.5 mmol/kg.

The patients had primary tumors that were detected histologically (N=9 with colorectal carcinoma, N=2 with intestinal carcinoid, N=1 with stomach carcinoma, N=1 with leiomyosarcoma and N=1 with ovarian cyst adenocarcinoma) and the metastases (N≦5) had been detected by contrast medium-enhanced CT within one month before the Gd-EOB-DTPA study. Exclusion criteria for the patients were:

Age under 18 years, anamnesis of severe or allergy-like side effects after administration of contrast media, prior administration of Gd-EOB-DTPA, administration of contrast media within 24 hours before the study, a transplanted organ, women before menopause, an operation or liver biopsy 24 hours before or after the study and patients with laboratory parameters that deviate greatly from the standard.

CT studies were made before and 10 minutes, 60 minutes and (N=5) 120 minutes after intravenous infusion of Gd-EOB-DTPA with a Siemens-Spiral CT. The entire liver was measured within 20–30 seconds of a pause in breathing. The table feed rate was 8 mm/sec, the collimation 8 mm.

Using a basis of pre-contrast and post-contrast images, two independent observers evaluated the number and size of the metastases qualitatively (excellent, good, moderate, minimal, no improvement) and quantitatively (measurement of the Houndsfield units).

The compatibility of Gd-EOB-DTPA was determined by determining the overall condition, the recording of vital parameters and a laboratory analysis of serum and urine parameters.

Results

After intravenous infusion of Gd-EOB-DTPA, a dose-dependent increase of the CT density of the healthy liver was found. FIG. 1 shows the time behavior of the CT density (Houndsfield units, HU) in the liver of patients with primary tumors that can be detected histologically after the beginning of an infusion of 0.2 (o), 0.35 (♦) or 0.5 mmol/kg of Gd-EOB-DTPA (Λ). The CT density in the liver metastases is depicted with symbol *.

The CT density of the metastases was unchanged. In addition, a visualization of the gallbladder and the bile ducts was possible.

The visualization of the metastases was improved in all dose groups after infusion of Gd-EOB-DTPA. It was excellent in the two upper dose groups. After the maximum dose, on the average, two additional metastases were discovered, which previously were not known. The average size of the smallest metastases found correspondingly decreased from 20.3 to 16.6 mm. In the case of one patient with a known metastasis in the right lobe of the liver, an additional lesion with a 7 mm diameter, which previously had not been found, was detected in the left lobe of the liver after Gd-EOB-DTPA.

The general compatibility of GD-EOB-DTPA was good. Only four mild or moderate side effects were observed. In two cases, the patients reported a burning sensation at the infusion site or retrograde therefrom, which persisted for a few seconds or minutes. Other side effects were nausea and a sensation of pressure in the epigastric region. The evaluation of the laboratory parameters produced no precise trend. In the case of three patients, slight increases of aspartate transferase and alaninamino transferase were found, which were probably caused, however, by the liver metastases.

In summary, it follows from Example 14 that Gd-EOB-DTPA represents a well-tolerated and effective liver or gallbladder contrast medium for CT.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a method of performing computer tomography of the liver and the biliary tracts, the improvement wherein a contrast agent is administered and said contrast agent is a metal complex is of formula IV

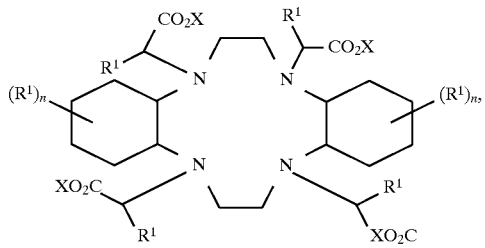
(IV)

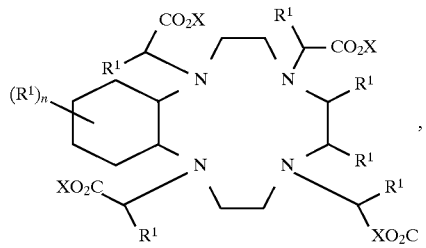
(V)

wherein

X is, in each case, independently of one another, hydrogen or a metal ion equivalent of an element of the atomic numbers 39–42, 44–51 or 56–83, n is 0, 1 or 2, $R^1$ is, in each case, independently of one another, hydrogen, or a radical of formula Ia

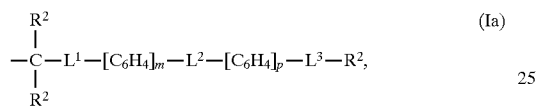
(Ia)

m and p are each independently 0 or 1, wherein at least one of m or p is 1, and if either m or p is equal to zero, two or more heteroatoms are not directly connected to one another, $R^2$ is, each case, independently of one another, hydrogen or a branched or unbranched, saturated or unsaturated $C_1$–$C_6$ hydrocarbon radical, and $L^1$, $L^2$ and $L^3$ are, in each case independently of one another, a direct bond, an oxygen atom, a sulfur atom, —N(H), —N($R^2$), a $C_1$–$C_{10}$ alkylene chain, or a $C_1$–$C_{10}$ alkylene chain interrupted by an oxygen atom, a sulfur atom, —N(H) or —N($R^2$).

wherein

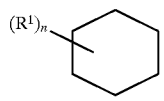

the symbol is a saturated, unsaturated or aromatic $C_6$ ring which is substituted n-fold by $R^1$, wherein free carboxyl groups that are not used for complexing can optionally be present as salts of physiologically compatible cations or as amides of the formula

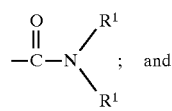
; and at least one of the $R^1$ groups is a radical of formula Ia.

2. In a method of performing computer tomography of the liver and the biliary tracts, the improvement wherein a contrast agent is administered and said contrast agent is a metal complex is of formula V wherein X is, in each case, independently of one another, hydrogen or a metal ion equivalent of an element of the atomic numbers 39–42, 44–51 or 56–83, n is 0, 1 or 2, $R^1$ is, in each case, of one another, hydrogen or a radical of formula Ia independently

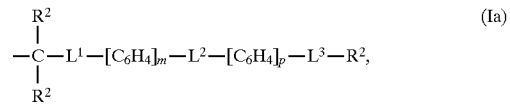
(Ia)

m and p are each independently 0 or 1, wherein at least one of m or p is 1, and if either m or p is equal to zero, two or more heteroatoms are not directly connected to one another, $R^2$ is, in each case, independently of one another, hydrogen or a branched or unbranched, saturated or unsaturated $C_1$–$C_6$ hydrocarbon radical, and $L^1$, $L^2$ and $L^3$ are, in each case, independently of one another, a direct bond, an oxygen atom, a sulfur atom, —N(H), —N($R^2$), a $C_1$–$C_{10}$ alkylene chain, or a $C_1$–$C_{10}$ alkylene chain interrupted by an oxygen carbon atom, a sulfur atom, —N(H) or N($R^2$);

wherein the symbol

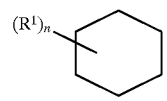

is a saturated, unsaturated or aromatic $C_6$ ring which is substituted n-fold by $R^1$, wherein free carboxyl groups that are not used for complexing can optionally be present as salts of physiologically compatible cations or as amides of the formula

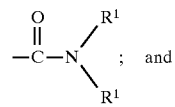
; and at least one of the $R^1$ groups is a radical of formula Ia.

3. In a method of performing computer tomography of the liver and the biliary tracts, the improvement wherein a contrast agent is administered and said contrast agent is a metal complex is of formula IV

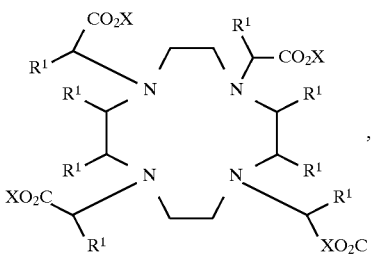

wherein
X is, in each case, independently of one another, hydrogen or a metal ion equivalent of an element of the atomic numbers 39–42, 44–51 or 56–83,
$R^1$ is, in each case, independently of one another, hydrogen, or a radical of formula Ia

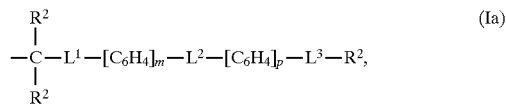

m and p are each independently 0 or 1, wherein at least one of m or p is 1, and if either m or p is equal to zero, two or more heteroatoms are not directly connected to one another,
$R^2$ is, in each case, independently of one another, hydrogen or a branched or unbranched, saturated or unsaturated $C_1$–$C_6$ hydrocarbon radical, and
$L^1$, $L^2$ and $L^3$ are, in each case, independently of one another, a direct bond, an oxygen atom, a sulfur atom, —N(H), —N($R^2$), a $C_1$–$C_{10}$ alkylene chain, or a $C_1$–$C_{10}$ alkylene chain interrupted by an oxygen atom, a sulfur atom, —N(H) or —N($R^2$);
wherein free carboxyl groups that are not used for complexing can optionally be present as salts of physiologically compatible cations or as amides of the formula

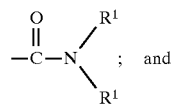

at least one of the $R^1$ groups is a radical of formula Ia.

4. A method according to claim 3, wherein said metal complex exhibits a stability constant of at least $10^{14}$ and a molecular weight of at most 1500 dalton.

5. A method according to claim 3, wherein said metal complex contains one or two radicals of formula Ia.

6. A method according to claim 3, wherein at least one of the radicals formula Ia is —$CH_2$—$C_6H_5$, —$CH_2$—$C_6H_4$—O—$CH_3$, —$CH_2$—$C_6H_4$—O—$CH_2CH_3$, —$CH_2$—$C_6H_4$—O—$C_3H_7$, —$CH_2$—$C_6H_4$—O—$C_4H_9$, —$CH_2$—$C_6H_4$—O—$C_5H_{11}$, —$CH_2$—$C_6H_4$—O—$CH_2$—$C_6H_5$, —$CH_2$—$C_6H_4$—$CH_3$, —$CH_2$—$C_6H_4$—$CH_2CH_3$, —$CH_2$—$C_6H_4$—$C_3H_7$, —$CH_2$—$C_6H_4$—$C_4H_9$ or —$CH_2$—$C_6H_4$—$C_5H_{11}$.

7. A method according to claim 3, wherein said metal is a metal of the lanthanoid series.

8. A method according to claim 3, wherein said metal is gadolinium, dysprosium, holmium, erbium, ytterbium or lutetium.

9. A method according to claim 3, wherein said metal is a metal of atomic numbers 72–83.

10. A method according to claim 3, wherein said metal is bismuth, lead or hafnium.

11. A method according to claim 3, wherein said metal is of atomic numbers 39–42.

12. A method according to claim 3, wherein said metal is of atomic numbers 44–51.

13. A method according to claim 3, wherein said physiologically compatible cations are selected from $Na^+$, $Ca^{2+}$, $Mg^{2+}$, $Zn^{2+}$ and cations of meglumine, glucosamine, arginine, ornithine, lysine or ethanolamine.

14. A method according to claim 3, wherein said metal complex has at least two carboxyl groups not involved in complexing of a metal ion equivalent of an element of atomic numbers 39–42, 44–51 or 56–83.

15. A method according to claim 3, wherein $R^4$ is, in each case, methoxybenzyl, ethoxybenzyl or butoxybenzyl.

16. A method according to claim 3, wherein X is, in each case, independently of one another, hydrogen or a metal ion equivalent of holmium, erbium, ytterbium, gadolinium or dysprosium.

17. A method according to claim 3, wherein X is, in each case, independently of one another, hydrogen or a metal ion equivalent of lutetium, praseodium, cerium, hafnium, lead or bismuth.

18. A method according to claim 3, wherein said metal complex is administered as an aqueous solution optionally containing one or more buffers, bases, acids, stabilizers, solubilizers, substances for matching osmolality, substances for matching viscosity, free complexing agents, and/or salts or complexes of complexing agents with weakly bound physiologically compatible ions.

19. A method according to claim 18, wherein said aqueous solution contains 0.1–10 mole %, relative to the diagnostically effective metal complex, of a free complexing agent or a salt or complex thereof with weakly bound physiologically compatible ions.

20. A method according to claim 19, wherein said weakly bound physiologically compatible ions are ions of calcium, magnesium or zinc.

21. A method according to claim 3, wherein said metal complex is administered in an amount of 0.1–1.5 mmol/kg of body weight.

22. A method according to claim 3, wherein said metal complex is administered in an amount of 0.2–0.6 mmol/kg of body weight.

23. A method according to claim 3, wherein said metal complex is administered by intravenous infusion or injection over a period of 1–30 minutes.

* * * * *